United States Patent [19]
Damodaran et al.

[11] Patent Number: 5,976,859
[45] Date of Patent: Nov. 2, 1999

[54] DETERGENT-STABLE ALKALINE PROTEASE FROM *BACILLUS PUMILUS*

[75] Inventors: Srinivasan Damodaran; Xiao-Qing Han, both of Madison, Wis.

[73] Assignee: Wisconsin Alumni Research Foundation, Madison, Wis.

[21] Appl. No.: 08/751,070

[22] Filed: Nov. 15, 1996

[51] Int. Cl.$^6$ .................................. C12N 9/54; C11D 7/42
[52] U.S. Cl. ........................ 435/221; 510/226; 510/300; 510/320; 510/392
[58] Field of Search .................................. 435/221, 222; 510/226, 300, 320, 392

[56] References Cited

U.S. PATENT DOCUMENTS

| | | | |
|---|---|---|---|
| 4,050,989 | 9/1977 | Kuwana et al. | 435/71.3 |
| 4,386,160 | 5/1983 | Branner-Jorgensen | 435/221 |
| 5,314,807 | 5/1994 | Yoshikawa et al. | 435/68.1 |
| 5,346,822 | 9/1994 | Vetter et al. | 435/221 |
| 5,427,936 | 6/1995 | Moeller et al. | 435/198 |
| 5,453,372 | 9/1995 | Vetter et al. | 435/222 |
| 5,457,045 | 10/1995 | Anker et al. | 435/201 |
| 5,478,742 | 12/1995 | Vetter et al. | 435/252.31 |
| 5,518,917 | 5/1996 | Boyer et al. | 435/252.5 |

FOREIGN PATENT DOCUMENTS 01101886  4/1989  Japan .

OTHER PUBLICATIONS

Bajorath, J.; Saenger, W. and Pal, G. P. 1988a. Autolysis and inhibition of proteinase K, a subtilisin–related serine proteinase isoloated from the fungus *Tritirachium album* limber. *Biochim. Biophy. Acta* 954:176–182.
Bajorath, J.; Hinrichs, W. and Saenger, W. 1988b. The enzymatic activity of proteinase K is controlled by calcium. *Eur. J. Biochem.* 176, pp. 441–447.
Chavira, R.; Burnett, T.; and Hageman, J. H. 1984. Assaying proteinases with azocoll. *Anal. Biochem.* 136, pp. 446–450.
Deane, S. M., Robb, F. T. and Woods, D. R. 1987. *J. Gen. Micro.* 133, pp. 391–399.
DelMar, E. G., Largman, C., Brodrick, J. W. and Geokas, M. C. 1979. A sensitive new substrate for chymotrypsin. *Anal. Biochem.* 99, pp. 316–320.
Ebeling, W.; Hennrich, N.; Klockow, M.; Metz, H.; Orth, H. D. and Lang, H. 1974. Protease K from *Tritirachium album* limber, *Eu J. Biochem.* 47:91–97.
Froömmel, C. and Höhne, W. E. 1981. Influence of calcium bind on the thermal stability of thermitase, a serine protease from *Thermoactinomyces vulgaris*. *Biochim. Biophys. Acta* 670:25–31.
Gold, A. M. 1967. Sulfonylation with Sulfonyl Halides. In *Methods of Enzymology*, Hirs, C. H. W. (ed), Academic Press, New York, vol. 11, pp. 706–711.
Jany, K. D.; Lederer, G. and Mayer, B. 1986. Amino acid sequence of protease K from the mold *Tritirachium album* limber. *FE Letters* 199(2):139–144.
LeGendre, N.; Mansfield, M.; Weiss, A. and Matsudaira, P. 1993 In *A Practical Guide to Protein and Peptide Purification for Microsequencing*, Academic Press, San Diego, pp. 71–101.

Nakanishi, T. and Yamamoto, T. (1974). *Agric. Biol. Chem.* (Tokyo) 38, pp. 2391–2397.
Nickerson, W. J. and Durand, S. C. (1963). *Biochim. Biophy. Acta*, 77, pp. 87–99.
Ottesen, M. And Svendsen, I. 1970. In *Methods in Enzymology*, ed. E. Perlmann and L. Lorand, Academic Press, New York, vol. 19, pp. 199–215.
Reimerdes, E. H. and Klostermeyer, H. 1976. In *Methods in Enzymology*, L. Lorand, Ed., Academic Press, New York. vol. 45, part B, pp. 26–28.
Schagger, H. and von Jagow, V. 1987. Tricine–Sodium Dodecyl Sulfate–Polyacrylamide Gel Electrophoresis for the Separation of Proteins in the Range from 1 to 100 kDa. *Anal. Biochem.* 166, pp. 368–379.
Smith, E. L.; DeLange, R. J.; Evans, W. H.; Landon, M. and Markland, F. S. 1968. Subtilisin Carlsberg. V. The Complete Sequence; Comparison with Sobtilisin BPN; Evolutionary Relationships, *J. Biol. Chem.* 243:2184–2191.
Teorell, T.; and Stenhagen, E. 1938. *Biochem. Z.* 299, pp. 416–419.
Tsong, T.Y.; Hearn, R.P.; Wrathall, D.P. and Sturtevant, J.M. 1970. A calorimetric study of thermally induced conformational transitions of ribonuclease A and certain of its derivates. *Bioche* 9:2666–2677.
Umezawa, H. 1976. Structures and activities of protease inhibitors of microbial origin. In *Methods of Enzymology*. Lorand L. (ed), Academic Press, New York. vol. 45, pp. 678–695.
Voordouw, G. and Roch, R. S. 1975. The Role of Bound Calcium ions in Thermostable, Proteolytic Enzymes. I. Studies on Thermomycolase, the Thermostable Protease from the Fungus. *Bioche* 14:4659–4666.
Yu, R. J., Harmon, S. R., Wachter, P. E. and Blank, F. (1969) *Arch. Biochem. Biophys.* 135, pp. 363–370.
Institute of Forestry and Pedology (1974) K'o Hsueh T'ung Pao, 19(1), "Alkaline Proteinase Preparation from *Bacillus pumilus*", pp. 34–37.
Tri Tran et al. (1975) Bromatol. Chem. Toksikol., 8(4), "Kinetic Studies on Alkaline and Serine Neutral Proteinase from *Bacillus pumilus*", pp. 439–446.
Qiu et al. (1990) Weishengwu Xuebao, 30(2), "Study on Alkaline Proteinase from Alkaliphilic *Bacillus pumilus*. II Research on the Selection of High Producing Strain and the Conditions for Enzyme Production".
Yang et al. (1994) Weishengwuxue Tongbao, 21(5), "The Construction of Alkaline Protease Producing Engineering Strain Using Starch as Raw Material from *Bacillus pumilus*", pp. 273–278.
Yumi et al. (1996) Nippon Seibutsu Kogakkai Taikai Koen Yoshishu, 1996, "Alkaline Protease from *Bacillus pumilus* MS–1", p. 200.

*Primary Examiner*—Jon P. Weber
*Attorney, Agent, or Firm*—DeWitt Ross & Stevens SC

[57] ABSTRACT

A detergent stable alkaline protease, its use and a method for producing the protease are described. The protease is isolated from *Bacillus pumilus*. The protease according to the invention is suitable for use in compositions for cleaning and washing purposes.

8 Claims, 15 Drawing Sheets

DETERGENT-STABLE ALKALINE PROTEASE FROM *BACILLUS PUMILUS*

This invention was made with United States government support awarded by USDA Grant No. 94-37500-0589. The United States government has certain rights in this invention.

FIELD OF THE INVENTION

The present invention relates to proteolytic enzymes in general and specifically to a novel extracellular alkaline protease from *Bacillus pumilus*, which is highly resistant to denaturing agents.

REFERENCE TO CITATIONS

Full bibliographic citations to the references cited in this application can be found in the Bibliography section preceding the claims.

BACKGROUND OF THE INVENTION

Thermostable and detergent compatible proteases are widely used in food and detergent industries. Common household detergents contain proteolytic enzymes, of which the majority are produced by the members of the genus Bacillus. Although subtilisins have long been the enzymes of choice for detergent formulations, they are not the ideal detergent enzymes because they possess low thermal stability in the presence of detergents and short shelf-life. Enzymes like this have been known for some time. For example, reference is made to the following patents.

U.S. Pat. No. 4,386,160 to Branner-Jorgensen describes a thermally de-stabilized Bacillus serine protease, modified such that the thermal stability is reduced to a level at which the proteolytic activity may be deactivated by a heat treatment.

U.S. Pat. No. 5,346,822 to Vetter et al. describes alkaline Bacillus proteases, their use and a method for producing these proteases. These are in particular Bacillus proteases from *Bacillus pumilus* DSM 5777.

U.S. Pat. No. 5,427,936 to Moeller et al. describes alkaline *Bacillus lipases* in combination with proteases, which are suitable for cleaning, washing and bleaching purposes.

An enzyme's resistance to denaturing agents, such as sodium dodecylsulfate (SDS) or urea, is one indication of strong proteolytic activity. Proteases withstanding 1% SDS without undergoing denaturation have commonly been considered as SDS-resistant. Proteases, such as alcalase from *B. licheniforms* and subtilisin from *B. subtilis*, have long been used in detergents. Deane et al (1987) reported a SDS-resistant protease but not a SDS-stable protease because the enzyme's proteolytic activity can be restored only after removing SDS. So far, proteinase K (EC 3.4.21.14) from fungal *Tritirachium album limber* has been considered as the most powerful microbial protease in terms of its stability against SDS. Proteinase K could still retain about 65% its original enzymatic activity in the presence of 6% SDS in its reaction system (Bajorath et al., 1988a).

Enzymes from various sources differ greatly in their catalytic and physical properties. Since it is still unclear so far about the exact function of each amino acid in contributing to the structure of proteins, artificial modification of proteins may not always produce expected results. While site-directed mutagenesis may provide information on the role of some specific amino acid side-chains in protein functionalities, wild-type proteins with some novel properties will give more information on structure-function relations and this in-turn will guide further mutagenic studies in protein science.

SUMMARY OF THE INVENTION

The present invention is directed to a substantially pure alkaline protease composition isolated from *Bacillus pumilus* and having an N-terminal amino acid sequence of A Q T V P Y G I P Q I K A P A V H A Q G Y K G A N V K V A V [SEQ. ID. NO. 1].

The present invention is directed to a new extracellular alkaline protease, termed protease Q, which is highly resistant to denaturing agents such as sodium dodecyl sulfate (SDS) or urea, and has been isolated from a strain of *Bacillus pumilus* screened from soil samples. Protease Q has an isoelectric point (pI) of 9.35 and is composed of 309 amino acids. Protease Q has a molecular weight of 31,100 daltons and is stable at pH values from 5.0 to 12.0. Protease Q is most active at pH 10.5.

The present invention is also directed to a cleaning composition comprising an isolated and substantially pure alkaline protease described above and preferably at least one conventional surface active detergent ingredient.

Some advantages of the enzyme of the present invention are that it is not easily denatured in SDS, urea and other denaturing agents at room temperature and shows strong proteolytic activity against all native proteins investigated including human keratin, yeast RNAase I, α-lactalbumin, and β-lactoglobulin. The presence of 1–2% (w/v) SDS enhances its proteolytic activity and it could only be denatured slowly in 10% SDS at temperatures greater than 50° C.

The protease according to the invention is useful as an additive for detergent and cleaning agent compositions. The invention therefore also relates to the use of the protease according to the invention in detergents and other cleaning agent, such as dish washing or laundry soap compositions. The invention is also directed to industrial cleaning operations, such as cleaning of ultrafiltration/microfiltration membranes in food and pharmaceutical industries. The protease of the present invention may also advantageously be used in the presence of other conventional enzymes, in particular in the presence of other proteases and lipases.

Further aims, objects, and advantages of the above-described multi-component value-added concentrate will become apparent upon a complete reading of the Detailed Description, drawings, and attached claims, below.

DETAILED DESCRIPTION OF THE INVENTION

Amino Acids

Figure 1:
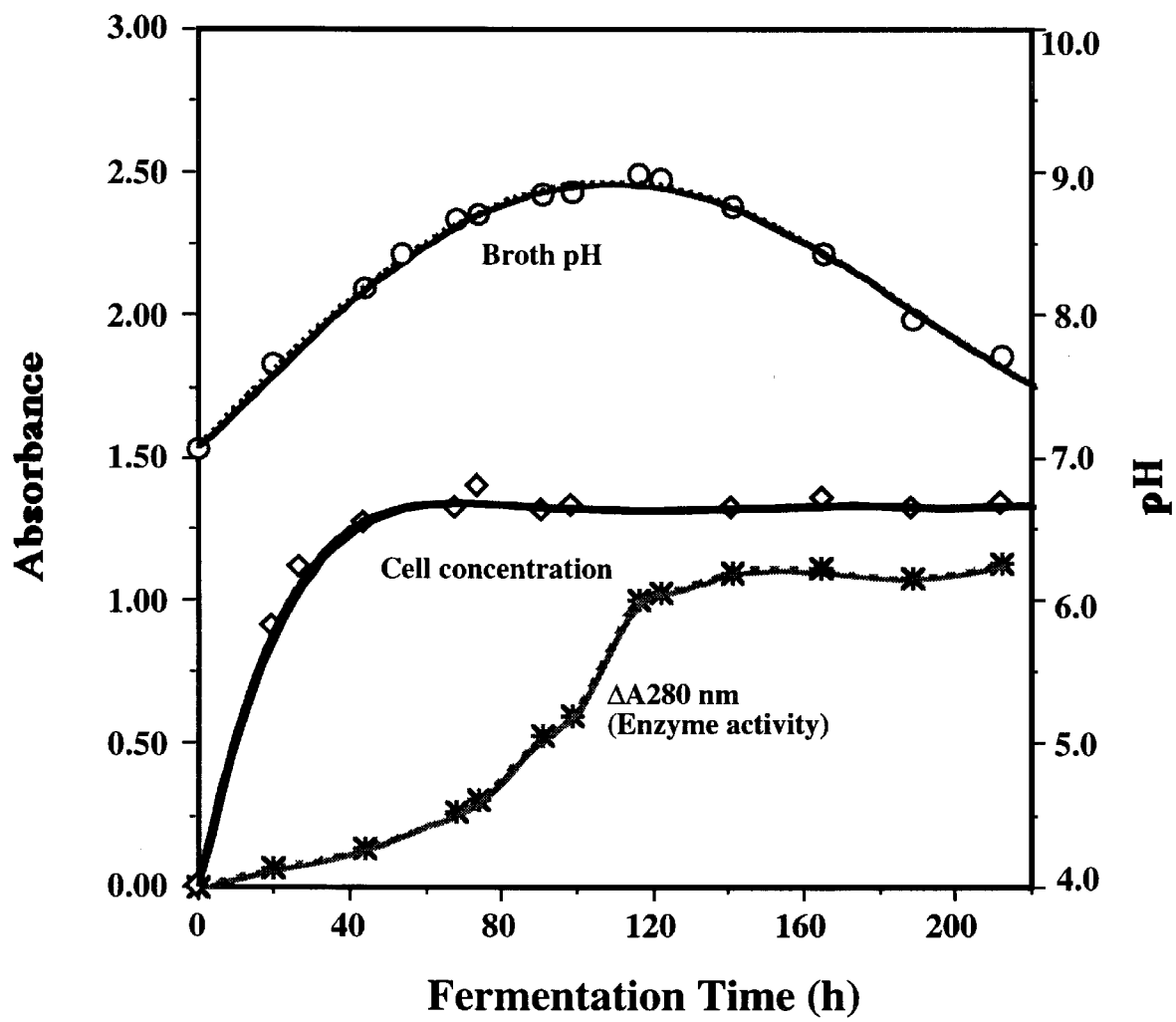
FIG. 1 is a graph showing the fermentation of *Bacillus pumilus*.

The following one or three-letter amino acid nomenclature conventions are used throughout the specification and claims:

| Abbreviated Designation | Amino Acid |
| --- | --- |
| A Ala | Alanine |
| C Cys | Cysteine |
| D Asp | Aspartic acid |
| E Glu | Glutamic acid |
| F Phe | Phenylalanine |
| G Gly | Glycine |
| H His | Histidine |
| I Ile | Isoleucine |
| K Lys | Lysine |
| L Leu | Leucine |
| M Met | Methionine |
| N Asn | Asparagine |
| P Pro | Proline |
| Q Gln | Glutamine |
| R Arg | Arginine |
| S Ser | Serine |
| T Thr | Threonine |
| V Val | Valine |
| W Trp | Tryptophan |
| Y Tyr | Tyrosine |

Protease Q, an SDS/urea-resistant alkaline protease from *Bacillus pumilus*, has been purified from fermentation broth showing a single band on silver-stained Tricine-SDS-PAGE gel. It is a basic protein having the following characteristics:

1) an isoelectric point (pI) of 9.35
2) composed of 309 amino acids
3) a molecular weight of 31,100 daltons
4) stable at pH values from 5.0 to 12.0
5) most reactive at pH 10.5
6) like all other bacterial subtilases, protease Q contains no disulfate bond in its structure
7) stability against denaturing agents such as SDS or urea
8) strong proteolytic activity on many native proteins including keratin and RNAase I
9) possesses neither esterase nor amidase activity on synthetic substrates with Arg at position 1, which are typical substrates of trypsin-like proteases
10) can only be inhibited irreversibly by serine protease inhibitors such as PMSF.

Many properties of protease Q are similar with that of proteinase K, a subtilisin-related serine protease isolated from fungus *Tritirachium album* limber (Ebeling et al., 1974). However, all results available so far indicate that protease Q is not a proteinase-K-like enzyme, but a new member of subtilisin family.

N-terminal Sequence and Amino Acid Composition:

N-terminal sequence and amino acid composition of the enzyme were determined by transblotting the enzyme protein from Tricine-SDS-PAGE gel to polyvinylidene difluoride (PVDF) membrane according to the method described by LeGendre (1993) and Findley and Geisow (1989) with slight modification. The Tricine-SDS-PAGE gel (16.5% T) was pre-run with 0.001 g thioglycolic acid in 100 mL running buffer for 10 min at 10 mA constant electric current before loading protein samples. Transblotting was performed in a Trans-Blot SD Semi-Dry Transfer Cell (BIO-RAD, CA) at 12 V constant voltage for 12 hours. The PVDF membrane with transblotted proteins was stained by Coomassie Blue-R for 5 min and destained by SDS-PAGE destaining solution for 5 min. The membrane was incubated with deionized water for 1 hr before the membrane was dried. The transblotted protein samples in the dried PVDF membrane were used for N-terminal sequencing and amino acid composition determination by Protein/Nucleic Acid Shared Facility, The Medical College Of Wisconsin, (Milwaukee, Wis.). The N-terminal amino acid sequence of protease Q was determined to be: A Q T V P Y G I P Q I K A P A V H A Q G Y K G A N V K V A V [SEQ. ID. NO. 1].

The N-terminal sequence of protease Q and that of two well-known main commercial proteases, subtilisin Carlsberg (produced by *Bacillus amyloliquefaciens*) and subtilisin BPN' (produced by *Bacillus licheniformis*) are shown below:

BPN': A Q S V P Y G V S Q I K A PA L H S Q G Y T G S N V K V A V [SEQ. ID. NO. 2]

Carlsberg: A Q T V P Y G I P L IKA DK V Q AQG F K G A N V K V A V [SEQ. ID. NO. 3]

Protease Q: A Q T V P Y G I P Q I K A P A V H A Q G Y K G A N V K V A V [SEQ. ID. NO. 1]

Protein data bank (SwissProt) search results indicate that the N-terminal sequence of protease Q is highly homologous with that of subtilisin Carlsberg. Further alignment of the N-terminal sequence of protease Q (from 1 to 30) with both subtilisin Carlsberg and subtilisin BPN' reveals that protease Q is exactly a hybridized product of the two enzymes. That is, at the locations where protease Q does not match with Carlsberg, it matches with BPN'. Without wishing to be restricted to any rationale for this phenomenon, it is believed that the amino acids missed in subtilisin Carlsberg but presented in subtilisin BPN' may be important for the high stability of protease Q in detergent solutions. It has been suggested that subtilisins (with 275 amino acids) may have evolved by a process of duplication of parts of the sequences resulting in the extension of a shorter peptide chain to the present longer ones (Smith et al., 1968). If this suggestion is true, then it can be said that the further longer peptide chain of protease Q (with 309 amino acids) came from those subtilases mentioned above.

Protease Q does not contain a cystine residue, indicating its trypsin-unrelated molecular structure. Since all known bacterial subtilisins, except the subtilisin from *Bacillus smithii,* lack disulfide bridges, whereas all trypsin-related enzymes contain such bonds (Jany et al., 1986), protease Q belongs to subtilisin-related protease according to its molecular structure. The most significant difference of the amino acid composition of protease Q is its Asx residues (i.e., Asp plus Asn residues) in comparing with other subtilisins or protease K. Protease Q contains 46 amino acid residues of Asx, corresponding to 14.8mole %. Protease K contains 11.2 mole % Asx; and subtilisin BPN' and subtilisin Carlsberg contain 10.2 and 9.45 mole %, respectively).

The amino acid composition is found in Table 1 as follows:

TABLE 1

Amino Acid Composition of Protease Q

| Amino Acid | Mole % | No. of Amino Acids |
|---|---|---|
| Asx | 14.83 | 46 |
| Thr | 5.01 | 15 |
| Ser | 9.83 | 30 |
| Glx | 5.34 | 17 |
| Pro | 5.57 | 17 |
| Gly | 11.38 | 35 |
| Ala | 13.09 | 40 |
| Val | 12.06 | 37 |
| Met | 1.14 | 4 |
| Ile | 4.00 | 12 |
| Leu | 5.650 | 17 |
| Tyr | 3.285 | 10 |
| Phe | 1.777 | 5 |
| His | 1.516 | 5 |
| Lys | 3.444 | 11 |
| Arg | 2.133 | 7 |
| Cys | n.d. | 0 |
| Trp | — | — |

Isoelectric Point:

Protease Q is a basic protein with a pI value of 9.35. The value of pI was determined by using preparative isoelectric focusing cell (BIO-RAD). Isoelectric focusing was performed using 2.0% Bio-Lyte ampholyte (pH 3–10 for first run, and pH 8.0–10.0 for all later-on runs) in a total volume of 60 mL. Focusing of the enzyme was performed for 3.5 hours at 15 W constant power supply at 1° C. Twenty fractions were harvested and their pH values, protein concentrations, as well as proteolytic activity measured. Fractions with proteolytic activity were pooled and the ampholyte removed by passing though a Sephacryl-100 gel filtration column.

Proteolytic Activity:

Protease Q demonstrated its proteolytic activity on a variety of proteins including, without limitation, keratin, RNAase I, bovine serum albumin (BSA), β-lactoglobulin, β-casein, 7 S and 11 S soybean proteins. Fragmentation of these proteins into several polypeptides by protease Q indicates that it is an endopeptidase.

Molecular Mass:

Electrophoresis techniques (Tricine-SDS-PAGE) were used to determine molecular mass of protease Q. Reference is made to the EXPERIMENT 6 (infra.) for a description of these techniques. Protease Q has a relative molecular mass of 33,000 dalton as judged by silver-stained SDS-PAGE as described in EXPERIMENT 6 and illustrated in FIG. 2.

According to its amino acid composition (Table 1, supra.), the molecular weight of protease Q is 31,100, similar to the results obtained from SDS-PAGE.

Stability Against SDS and Other Surfactants:

Protease Q demonstrates that its property of SDS-resistance is at least comparable to that of proteinase K. On native protein substrates, protease Q demonstrates its stronger proteolytic activity in the presence of SDS as described in EXPERIMENTS 12–13 and illustrated in FIGS. 8–12.

Effect of Inhibitors:

Protease Q is not inhibited by the commonly used aspartyl protease inhibitor (Umezawa, 1976). Additionally, because protease Q does not contain any disulfide bond or free thiol residue according to the result of its amino acid composition (Table 1, supra.), neither N-ethyl maleimide (NEM) nor 2-mercaptoethanol has an effect on the activity of protease Q. Further, protease Q is not inhibited by inhibitors of trypsin-like enzyme, such as tosyl-lysine chloromethyl ketone (TLCK) and soybean trypsin inhibitor (SBTI), indicating its trypsin-unrelated catalytic characteristics. The enzyme is also not sensitive to leupeptin—inhibitor of trypsin-like serine proteases and most cysteine proteases (Umezawa, 1976). Although protease Q shows its strong amidase activity on succinyl-Ala-Ala-Pro-Phe-p-nitroanilide (AAPF) as mentioned in EXPERIMENT 5, it is insensitive to tosylamido-2-phenylethyl chloromethyl ketone (TPCK)—inhibitor of chymotrypsin-like enzymes, suggesting that it is not a chymotrypsin-like enzyme. However, like all other serine proteases, protease Q irreversibly loses its proteolytic activity with the presence of 1.0 mM of phenylmethylsulfonyl fluoride (PMSF) in the buffer system, indicating the involvement of serine in the mechanism of the enzyme's action (Gold, 1967). The irreversible inhibition (the activity of the enzyme could not be restored after the addition of reducing agent) of protease Q by PMSF indicates that it is a serine-type peptidase.

With the presence of ethylenediamine tetraacetic acid (EDTA), inhibitors of metaloprotease (Powers and Harper, 1986), the activity of protease Q is reduced to 79% of its original value. No further reduction of the enzyme activity is observed, indicating that protease Q is not a metallopeptidase. The presence of EDTA in the reaction system chelated metal ions, such as calcium, is responsible for maintaining an active conformation of the enzyme. The removal of calcium from the enzyme changes its conformation to a less active state, i.e., 79% of its original activity.

Results of calcium stabilization of protease Q show that the stability of protease Q was significantly enhanced with the presence of calcium in buffer system. Although the addition of calcium did not increase its proteolytic activity, the stability of protease Q is significantly decreased with the removal of calcium-EDTA complex by passing through a Sephadex G-25 gel filtration column after the addition of EDTA. As found for other subtilases (Tsong et al, 1970; Voordouw and Roch, 1975; Frömmel and Höhne, 1981; Bajorath et al., 1988b), calcium protects against autolysis and increases the thermal stability of protease Q.

Uses of Protease Q:

The protease according to the invention may be used in detergent and cleaning agent formulations, for instance as a cleaning composition in powdered detergent formulations, individually or if desired in combination, optionally also in combination with detergent and cleaning agent proteases of the prior art or other enzymes which are conventional in such compositions, such as proteases, amylases, lipases, pectinases, nucleases, oxido-reductases, cellulases etc.

In addition to the detergent enzymes already mentioned, the protease of the present invention may contain all the detergent constituents which are conventional in the prior art, such as surfactants, bleaching agents or builders, and also additional conventional adjuvants for detergent formulations in conventional quantities. Examples of adjuvants include intensifiers, enzyme stabilizers, anti-redeposition agents and/or compatibility agents, complexing and chelating agents, foam regulators and additives such as optical brighteners, opacifying agents, corrosion inhibitors, anti-electrostatic agents, dyes, bactericides, bleaching agent activators, and/or peracid bleaching agent precursors.

Method of Producing the Protease of the Present Invention:

The protease according to the invention is obtained by cultivating *Bacillus pumilus* or a microorganism containing the genetic information for protease Q according to the invention and subsequently isolating the resulting alkaline protease from the culture medium. The isolation of the alkaline proteases from the culture medium is carried out in known manner, in that the cells are separated by filtration or centrifugation, the protease is concentrated by membrane filtration or precipitation, purified, optionally isolated, and dispatched to its intended use.

The invention also comprises a method for producing the protease according to the invention. An exemplary method is described in U.S. Pat. No. 5,346,822 to Vetter et al., which is incorporated herein by reference to describe the particular method. Summarizing the method, the protease is produced with transformed microorganisms which contain an expression vector with DNA sequences which are required for protease expression and with a DNA sequence which codes for the amino acid sequence or an variation of the amino acid sequence of protease Q according to the invention. The microorganism thus transformed is cultivated as stated below, and the alkaline protease is isolated from the culture medium. The transformed microorganism for producing and obtaining the protease can be either a Bacillus species, most notably *Bacillus subtilis*, or any other organism.

The invention is further illustrated in the following experiments which are not intended to be in any way limiting to the scope of the invention as claimed.

EXPERIMENTS

The following procedures were common throughout the experimental protocol:

Materials:

Soil samples were collected from several locations in Wisconsin, Illinois, Iowa and New Mexico. Casein substrate, and other chemical reagents were purchased from Sigma Chemical Co. (St. Louis, Mo.). All chemicals and reagents used in this study were of analytical grade.

Screening and Fermentation:

All purpose agar from DIFCO (Chicago, Ill.) was used as plate culture for screening microorganisms. An aqueous extract of the soil was spread on agar plate and incubated at 37° C. for 24 hours. Four to six single colonies from the spread agar plate were selected and grown in broth by aerobic fermentation at 37° C. for 40 hours in 250 mL conical flasks using a fermentation medium containing 1.8% peptone, 0.2% $K_2HPO_4$, 0.1% $MgSO_4$, 0.3% yeast extract, 0.02% antiform reagent. The initial pH of the medium was 7.06. The flasks were shaken in an environmental shaker at 130 rpm. Growth rate was monitored by measuring turbidity of the medium at 610 nm. The fermentation broths were tested for proteolytic activity in SDS solutions.

One of the bacterial strains producing a highly active protease in SDS (detergent) solutions was identified. The bacterial strain, a Gram positive, rod-shaped, endospore-forming aerobic organism was identified as *Bacillus pumilus* according to its cell wall fatty acid composition as well as its other physiological properties. This *B. pumilus* strain, which is the preferred organism from which to isolate the alkaline protease described herein, has been deposited with the American Type Culture Collection, 12301 Parklawn Drive, Rockville, Md. 20852 (in accordance with the terms of the Budapest Treaty) and assigned Accession No. ATCC 202073.

Fermentation Kinetics:

FIG. 1 shows the growth curve of the isolated *Bacillus pumilus* strain and the time-dependent increase of extracellular proteolytic activity. To determine this activity, the fermentation medium (100 mL) in a 250 mL conical flask was incubated with vegetative cells. At each of the times indicated by the data points, 1 mL of the broth was removed and the cell growth (as determined by turbidity at 610 nm), the pH, the TCA (trichloroacetic acid) soluble polypeptides, and the proteolytic activity of the cell-free suspension were determined. The TCA soluble polypeptides were determined by centrifuging TCA precipitated suspension (broth/12% TCA=1/1) and reading changes in absorbance at 280 nm. Proteolytic activity was determined by using casein as substrate as described infra. Data are mean values of duplicated determinations.

Proteolytic activity in the fermentation broth appeared when the organism approached its stationary growth phase (around 40 hr) and the activity reached a maximum level after 100 hr as illustrated in FIG. 1. The proteolytic activity remained constant thereafter during the prolonged fermentation, suggesting that the enzyme was relatively stable against autolysis in the medium at 37° C. The pH of fermentation broth increased to a maximum value of 9.0 and then returned to its original pH level during a period of ten days fermentation. The time at which the pH reached a maximum during fermentation coincided with the time at which the enzyme concentration reached a stationary value. Thus, the pH of the fermentation broth can be conveniently used to monitor the progress of fermentation.

One unit of proteolytic activity was defined as the amount of enzyme which increased the absorbance at 280 nm (1 cm light path) of TCA-soluble protein hydrolysate of a casein solution by 0.001 units per min in the test. On this basis, the average yield for the production of protease Q was about 550 units per mL of fermentation broth after 110 hours of growth.

The enzyme in the fermentation broth was purified, according to the procedure described infra, to homogeneity (showing a single band on silver-stained SDS-PAGE gel) and used for all later experiments.

EXPERIMENT 1

Isolation and Purification of Protease Q

All isolation and purification steps were carried out at 5° C. if not mentioned specifically. The fermentation broth was centrifuged at 12,100 g for 20 min and the clear supernatant was directly mixed with diethyl amino ethyl (DEAE)-Sephadex A-50 ion exchange beads which had been previously equilibrated with 20 mM Tris-HCl buffer, pH 7.5 mM $CaCl_2$ (Buffer A). The suspension was filtered and the filtrate was concentrated by freeze-drying or by other means, such as ultrafiltration. The freeze-dried sample was dissolved in 20 mM Tris-HCl buffer, pH 8.3 containing 1 mM $CaCl_2$ (Buffer B) and fractionated by gel permeation chromatography on a Sephadex G-75 column using the above solvent as the eluent. It was found that the purity of the enzyme after this step was higher than 70%. The fractions with alkaline protease activity were collected and loaded on a Blue-Sepharose column. The column was eluted with 20 mM Tris-HCl buffer, pH 8.3 containing 1 mM $CaCl_2$ until the absorbance at 280 nm of the eluent approached zero. The column was then eluted with a NaCl gradient (from 0 to 0.2M) in the above Tris-HCl buffer. The fractions with alkaline protease activity were collected. The protease Q thus purified had a 171-fold purity compared to the activity in the original fermentation broth as shown in Table 2.

TABLE 2

Purification of Alkaline Protease*

| Samples | Vol (mL) | Proteins (mg/mL) | Activity (U/mg) | Yield (%) | Purification (folds) |
|---|---|---|---|---|---|
| Broth centrifugate | 100 | 20.2 | 25.1 | 100.0 | 1.0 |
| Ion-exchange column | 250 | 0.22 | 611 | 66.3 | 24.3 |
| G-75 Gel permeation | 60 | 0.23 | 2319 | 63.1 | 92.4 |
| Blue agarose column | 80 | 0.084 | 4294 | 56.9 | 171 |

*Proteolytic activity of the enzyme was determined by using casein as a substrate as described in EXPERIMENT 2. Data are mean values of duplicate determinations.

Protease Q was further purified by preparative isoelectric focusing (IEF). Fractions with alkaline protease activity were pooled and passed through a Sephacryl-G-100 gel permeation column using 20 mM Tris-HCl buffer, pH 8.3 containing 1 mM $CaCl_2$ as the eluent. The highly purified enzyme was stored under −80° C. for later use. Experiments with aqueous solutions of purified protease Q indicated that more than 70% of the enzyme's original activity remained even after incubation for 4 days at 37° C., indicating that the enzyme was stable in solution against autodigestion.

Alternatively, protease Q was isolated to a reasonably high purity using the following protocol: The fermentation broth was centrifuged at 12,100 g for 20 min and to the clear supernatant was added sodium sulfate crystals to a final value of 200 g/L. The solution was centrifuged at 12,100 g for 20 min. The supernatant was collected and stored in a cold room (4° C.) overnight. The sodium sulfate crystals formed were removed by filtration. The filtrate was mixed with acetone at a ratio of 1.0:1.5. The precipitated protein was removed by filtration and air dried. The acetone precipitated sample was then dissolved in Buffer A and the solutions was directly mixed with diethyl amino ethyl (DEAE)-Sephadex A-50 ion exchange beads which had been previously equilibrated with Buffer A. The suspension was filtered and the filtrate was concentrated by freeze-drying. This alternate isolation protocol also gave a highly pure protease Q preparation.

EXPERIMENT 2

Assay of Proteolytic Activity—Casein as a Substrate

Proteolytic activity using casein as a substrate was determined as described by Reimerdes and Klostermeyer (1976) with slight modification. The reaction mixtures were composed of 0.1 mL enzyme solution, 0.5 mL Buffer B, and 0.3 mL 1.5% of casein solution. The reaction mixtures were incubated at 37° C. for 20 min and the reaction stopped by the addition of 0.5 mL of 12% (w/v) TCA. Absorbance of TCA soluble materials was read at 280 nm after incubating the suspension in ice box for 15 min followed by centrifugation at 14,000× g for 10 min. One proteolytic unit was defined as the amount of enzyme which increased the absorbance at 280 nm of TCA-soluble protein (casein) hydrolysate by 0.001 unit per min in the test.

EXPERIMENT 3

Assay of Proteolytic Activity—Azoalbumin as a Substrate

Proteolytic activity using azoalbumin as a substrate was determined as described by Bajorath et al. (1988a) using the following protocol: The reaction mixtures were composed of 0.020 mL of enzyme solution, 0.28 mL of azoalbumin in 0.1 M Tris-HCl buffer (pH 8.8). The final concentration of azoalbumin in the reaction mixture was 0.2% (w/v). The reaction mixtures were incubated at 25° C. for 10 min and the reaction stopped by the addition of 0.3 mL of 12% (w/v) TCA containing 20%(v/v) ethanol. The TCA/ethanol stopped reaction mixtures were kept in ice for 15 min and then centrifuged at 14,000× g for 3 min. A 0.4 mL of the centrifuged supernatant was mixed together with the same volume of 2.0 M NaOH and its absorbance was read at 440 nm. One proteolytic unit was defined as the amount of enzyme which increased the absorbance at 440 nm of TCA/ethanol-soluble protein hydrolysate by 0.001 unit per min in the test.

EXPERIMENT 4

Assay of Proteolytic Activity—Azocoll as a Substrate

Proteolytic activity on Azocoll, an azo-dye impregnated collagen, was determined as described by Chavira et al. (1984) using the following protocol: The reaction mixture (0.6 mL) containing 0.5% azocoll, 0.05 mL enzyme solution in buffer B was incubated at 37° C. on a Tube Rocker shaking for a certain time. The reaction was stopped by centrifuging the reaction mixture for 1 min and immediately mixing (1:1) its supernatant with 0.2 M acetate buffer (pH 3.0). The proteolytic activity was expressed as increase in absorbance at 520 nm. All assays were completed with duplicated control and at least triplicate measurements.

EXPERIMENT 5

Assay of Proteolytic Activity Synthetic Oligopeptide as a Substrate

Amidase activity of the enzyme on synthetic oligopeptide was determined using succinyl-Ala-Ala-Pro-Phe-p-nitroanilide (AAPF)(SEQ. ID. NO: 4) as a substrate according to the method described by DelMar et al. (1979). The reaction was carried out in a 1.0 mL cuvette at 25° C. Absorbance at 410 nm was recorded immediately after the addition of 0.07 mL of 1.0 M AAPF to 0.63 mL of enzyme solution in 50 mM Tris-HCl buffer, pH 8.8. The amidase activity was determined from the initial velocity of the reaction. One unit of amidase activity was expressed as the amount of enzyme which can liberate 1.0 mM of p-nitroaniline per minute or reaction in the test. The amount of p-nitroaniline was evaluated by using a molar absorption coefficient of 8480 at 410 nm.

EXPERIMENT 6

Electrophoresis

Two electrophoresis techniques, Tricine-SDS-PAGE and gelatin-SDS-PAGE, were used. Tricine-SDS-PAGE was performed on a slab gel using a discontinuous Tricine (N-tris-[hydroxymethyl]-methylglycine) buffer system as described by Schagger and von Jagow (1987) for detecting low molecular weight proteins. The gel, after running, was fixed for 30 min (60 min for 1.5 mm gel) and stained with either Coomassie Blue-G or silver stain.

Figure 2A:
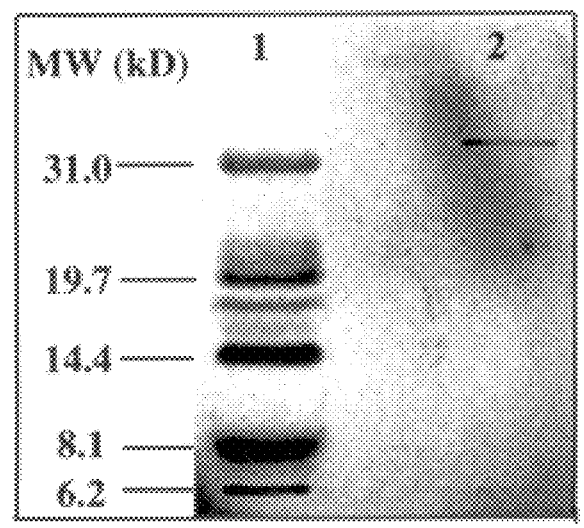
FIG. 2A is a computer-generated photograph showing a silver-stained sodium dodecylsulfate polyacrylamide gel electrophoresis (SDS-PAGE) gel of purified protease Q.
Figure 2B:
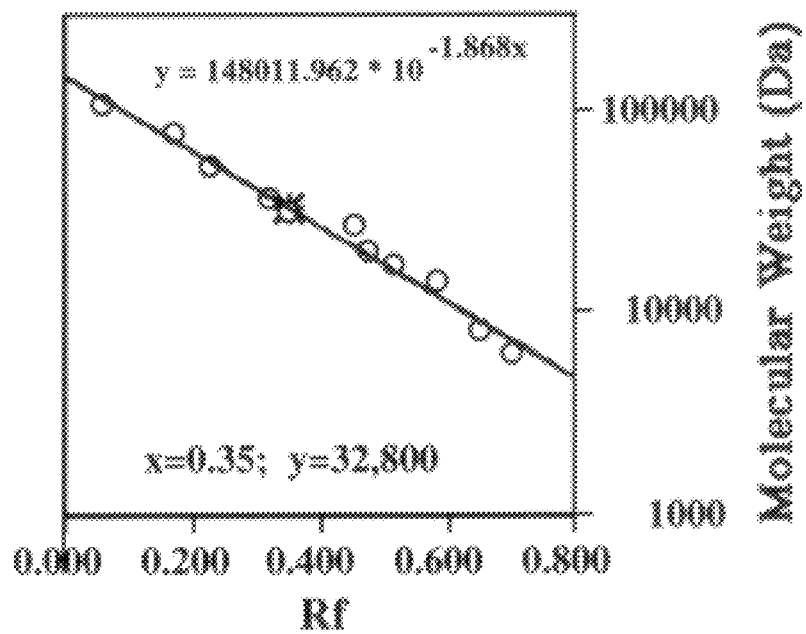
FIG. 2B is a graph showing the molecular weight of protease Q based on the electrophoretic mobilities ($R_f$) of standard proteins on the SDS-PAGE.

Protease Q is a basic protein with a pI value of 9.35 and a relative molecular mass of 32,800 Dalton as judged by silver-stained Tricine-SDS-PAGE, illustrated in FIG. 2, which is a SDS-PAGE gel (12.5% T) picture of protease Q stained with silver stain. In FIG. 2, lane 1 shows the protein markers and lane 2 shows protease Q. The right panel shows a typical plot of the relationship between molecular weight and mobility of protein standards and protease Q on the SDS-PAGE gel.

EXPERIMENT 7 pH Stability and Optimal Reaction pH of Protease Q

Figure 3:
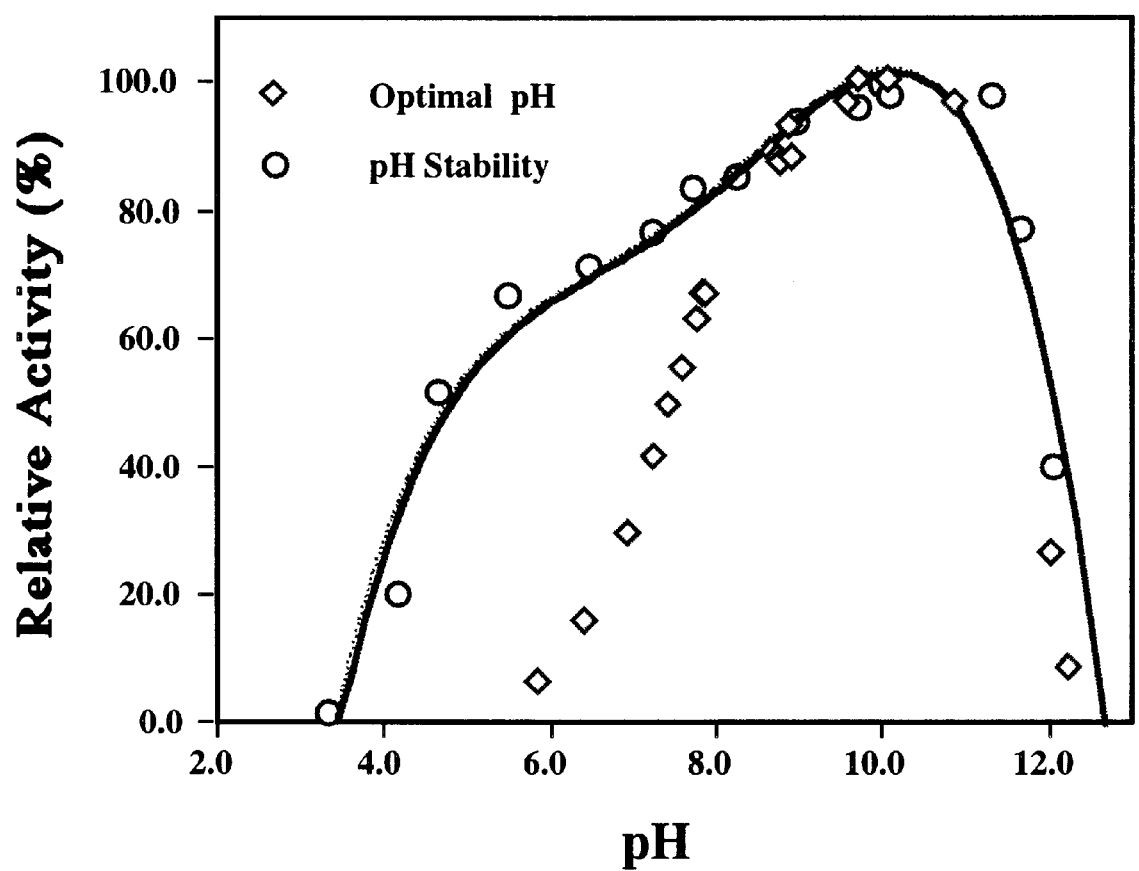
FIG. 3 is a graph showing the pH stability and optimal reaction pH of protease Q.

The universal buffer (5 mM) described by Teorell and Stenhagen (1938) was used to vary the pH (as the activity of protease Q was not significantly effected by ion-strength at I<0.5). For the determination of pH optimum of protease Q, the activity was determined at various pH. For the determination of pH stability, the enzyme solution (0.1 mL) was mixed with 1.0 mL of buffer at various pH. The mixtures were incubated at 25° C. for 120 min; an aliquot of the solution was then used to determine the proteolytic activity in Buffer B (pH 8.3) using casein as substrate, as described in EXPERIMENT 2. For the pH stability data, the pH values indicated in FIG. 3 are the initial pH values of the reaction mixture. Data are mean values of duplicate measurements. Protease Q is stable over a broad range of pH values (from pH 5.0 to around 12.0), and exhibits its proteolytic activity over a range of pH 7.5 to 11.5 as illustrated in FIG. 3, which shows the pH stability and optimal reaction pH of protease Q.

The optimal reaction pH is around 10.0 to 10.5 for the hydrolysis of casein under a 30 minute reaction at 37° C. No proteolytic activity was detected at pH values lower than 6.0, although the enzyme is stable down to pH 4.5. At pH 7.5, protease Q is stable for hours at 50° C. However, the enzyme became unstable at temperatures higher than 50° C.

EXPERIMENT 8

Optimal Reaction Temperature of Protease Q Using Azoalbumin as a Substrate

Figure 4:
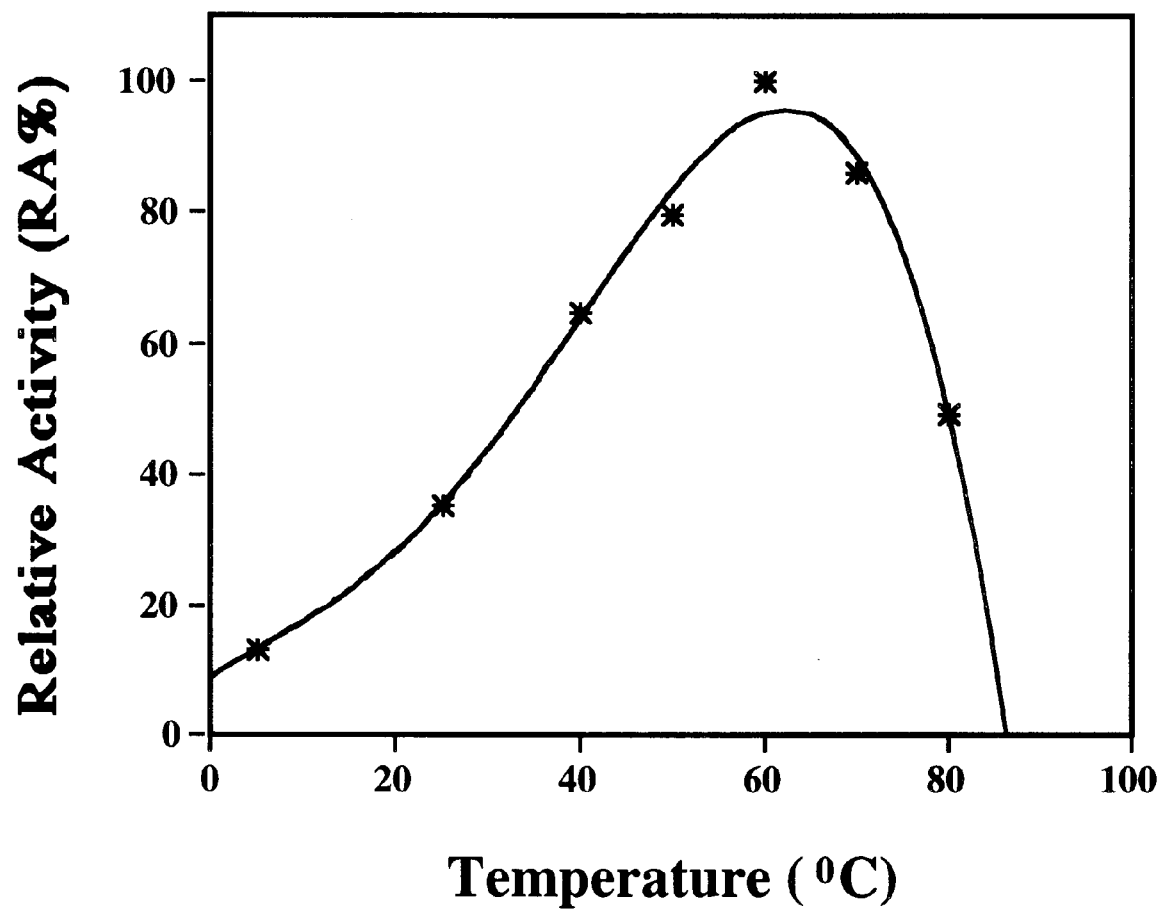
FIG. 4 is a graph showing the optimal reaction temperature of protease Q.

The activity of protease Q was determined as a function of reaction temperature by using azoalbumin as a substrate and a reaction time of 6 min (see EXPERIMENT 3). Data are mean values of duplicate measurements. The optimal reaction temperature is around 55° C. as illustrated in FIG. 4, which is similar to that of other alkaline proteases from Bacillus species.

EXPERIMENT 9

Thermal Stability of Protease Q Using Azoalbumin as a Substrate

Figure 5:
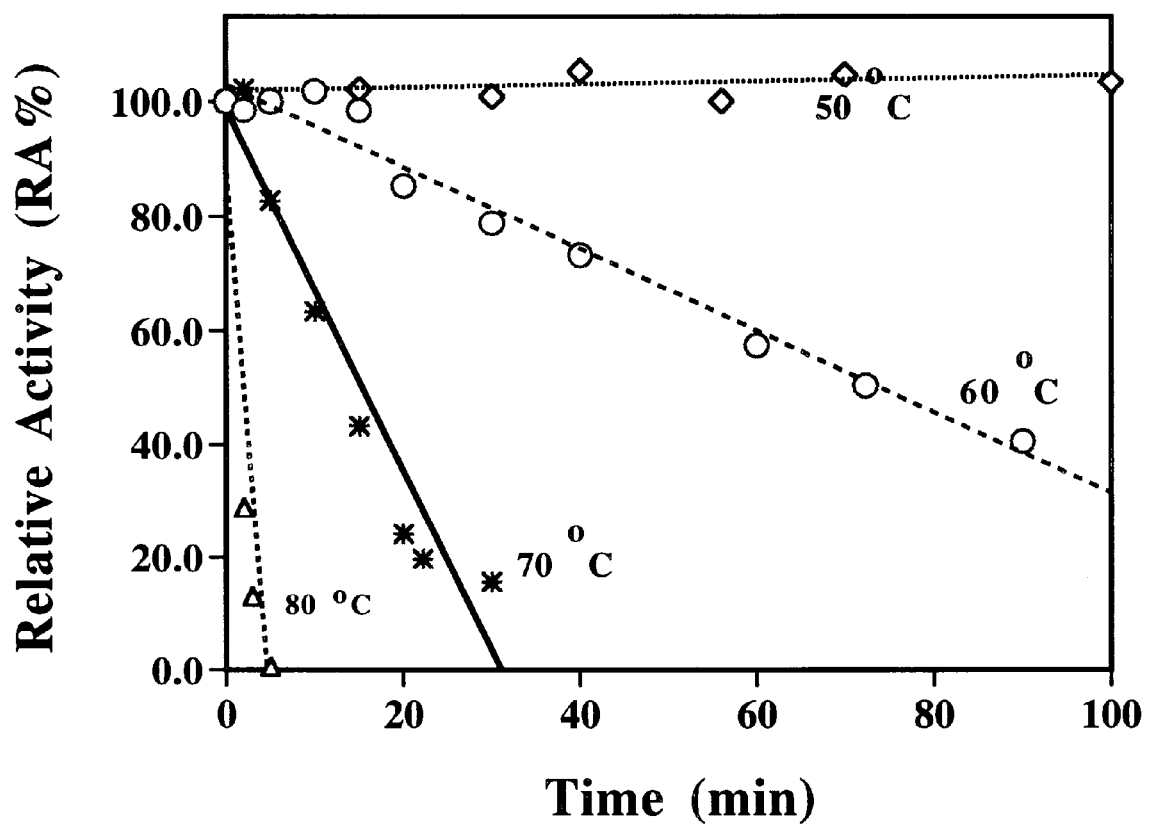
FIG. 5 is a graph showing the thermal stability of protease Q.

To determine the thermal stability, solutions of protease Q were incubated at various temperatures (indicated in FIG. 5) for various time intervals. The solutions were then cooled to 25° C. and the residual activity was determined at 25° C. using azoalbumin as a substrate as described in EXPERIMENT 3, but using a reaction time of 6 min. Data are mean values of duplicate measurements. When protease Q was incubated at 50° C., there was no reduction in its activity even after 100 min of incubation as illustrated in FIG. 5. The half-lives of protease Q at 60, 70, and 80° C. were about 60, 16, and 2 min, respectively, as illustrated in FIG. 5. The results of FIGS. 4 and 5 show that protease Q has maximum activity at 55° C. without any loss of stability for an extended period of time.

EXPERIMENT 10

Figure 6:
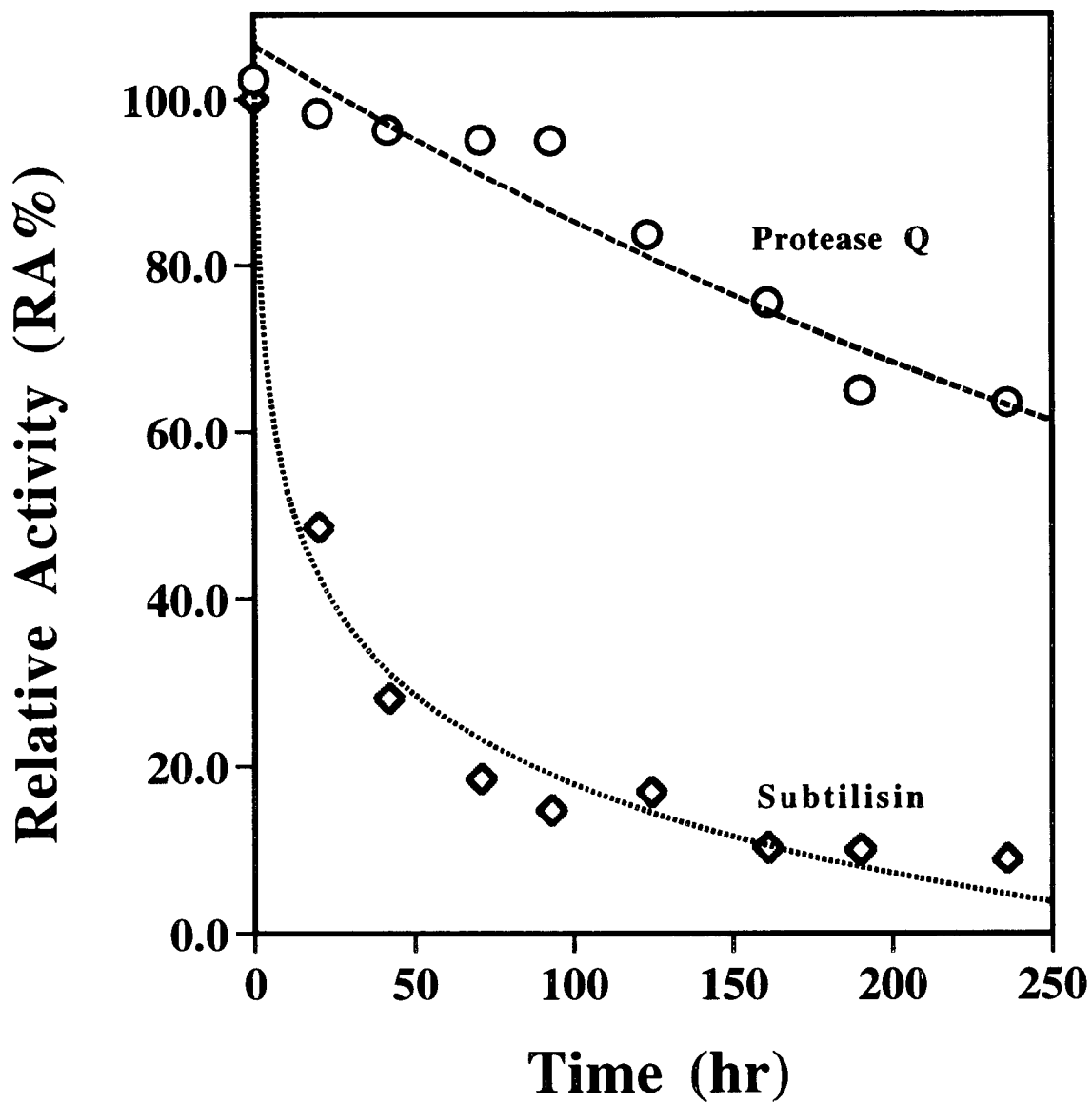
FIG. 6 is a graph showing the stability of protease Q and subtilisin Carlsberg against autolysis at 25° C., pH 7.5.

Comparison of Stability of Protease Q and subtilisin Carlsberg Against Autolysis Using Succinyl-Ala-Ala-Phe-Leu-p-Nitroanilide (AAPF) as a Substrate To determine the stability of protease Q against autolysis, the enzyme solution (pH 7.5) alone was incubated at 25° C. Aliquots were withdrawn at various time intervals and the residual activity of the enzyme was determined using succinyl-Ala-Ala-Phe-Leu-p-nitroanilide (AAPF) (SEQ. ID. NO: 4) as a substrate as described in EXPERIMENT 5. In this particular case, the residual activity represents the initial rate of hydrolysis of the substrate at 25° C. Data are mean values of duplicate measurements. The stability of protease Q against autolysis was compared with that of subtilisin Carlsberg under identical experimental conditions. As reported by Ottesen and Svendsen (1970), subtilisin molecules are not completely stable at any pH value although a solution containing 10–20% autolysis peptides can be kept with constant activity for many hours. At room temperature (pH 7.5), the half-life of protease Q is 328 hr, while commercial subtilisin Carlsberg lost half of its activity during the first day's incubation as illustrated in FIG. 6, which shows the stability of protease Q and subtilisin Carlsberg at 25° C. In terms of its stability against autolysis, protease Q is much more stable than that of subtilisin Carlsberg. Results obtained so far indicated that protease Q is reasonably stable at temperatures lower than 50° C., such as room temperature or at 37° C. However, at temperature higher than 50° C., protease Q lost its activity mostly due to autolysis.

EXPERIMENT 11

Proteolytic Activity of Protease Q on Keratin, RNAase, α-lactalbumin (LA) and g-globulin (GB)

The effect of protein substrate conformation on its digestion by protease Q was examined by using various protein substrates that represented various classes of proteins, such as albumins, globulins, and fibrous proteins. The reactions were performed according to EXPERIMENT 2 using 1% protein substrate in 0.1 M Tris-HCl buffer (pH 8.3). The enzyme to substrate ratio in the reaction mixture was 10 units of enzyme (on the basis of casein as substrate) per mg of protein substrate. The reaction mixture was incubated for 30 min at 37° C. To determine the effect of SDS on protease Q activity, digestion reactions were performed in the presence and in the absence of 2% SDS (w/v) in the reaction mixture. At the end of the reaction time, an aliquot of the reaction mixture was mixed with SDS-PAGE sample buffer containing 4% SDS and heated in a boiling water bath for 5 min to stop the reaction. The samples were then analyzed by SDS-PAGE (16.5% gel) as described in EXPERIMENT 6.

Figure 7A:
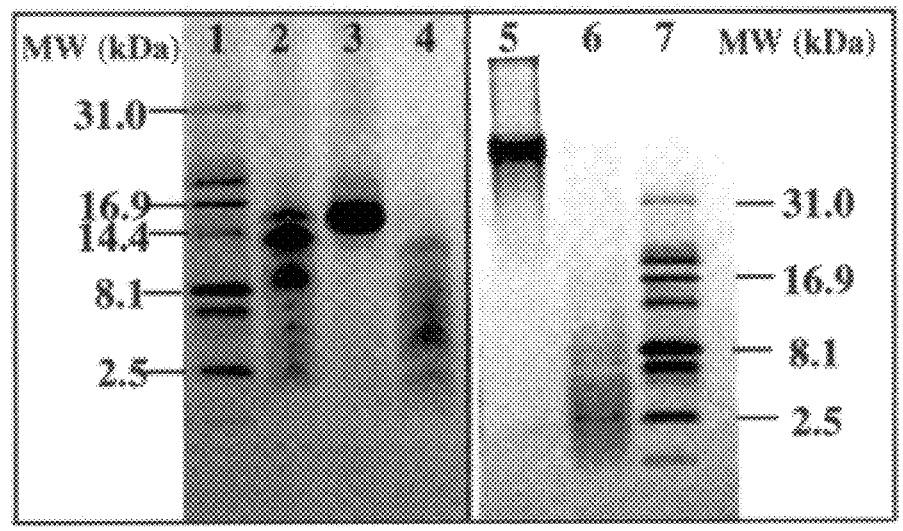
FIG. 7A is a SDS-PAGE gel showing proteolytic digestion of Keratin and RNAase by protease Q.

FIG. 7A illustrates the proteolytic activity of protease Q on Keratin and RNAase I. Lanes 1 and 7: standard protein markers; Lane 2: yeast RNAase I hydrolyzed by protease Q without the presence of SDS; Lane 3: yeast RNAase I control; Lane 4: RNAase I hydrolyzed by protease Q in the presence of 2% (w/v) SDS; Lane 5: human keratin control; Lane 6: keratin hydrolyzed by protease Q without the presence of SDS.

Figure 7B:
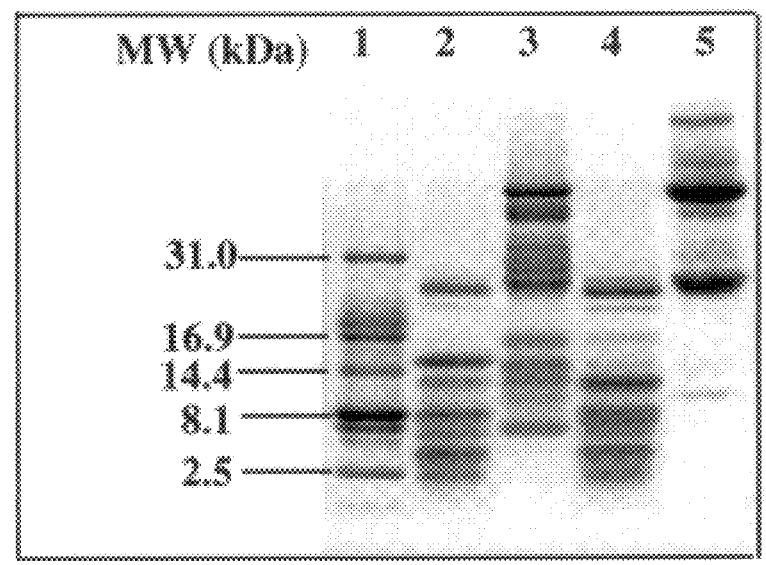
FIG. 7B is a SDS-PAGE gel showing proteolytic digestion of α-lactalbumin (LA) and γ-globulin (GB) by protease Q.

FIG. 7B illustrates the proteolytic activity of protease Q on α-lactalbumin (LA) and egg γ-globulin (GB). The experimental conditions were same as for FIG. 7A except that the reaction time was 40 min. Lane 1: LA hydrolyzed by protease Q in the presence of SDS; Lane 2: LA hydrolyzed by protease Q in the presence of 2% SDS and 1% (v/v) 2-mercaptoethanol; Lane 3: LA control; Lane 4: GB control; Lane 5: GB hydrolyzed by protease Q in the presence of 2% SDS plus 1% (v/v) 2-mercaptoethanol; Lane 6: GB hydrolyzed by protease Q in the absence of SDS; Lane 7: GB hydrolyzed by protease Q in the presence of 2% SDS.

Summarizing this experiment, protease Q demonstrated its proteolytic activity on the following native proteins which are structurally very different from each other: RNase I (FIG. 7A, Lane 2, 3, & 4), human keratin (FIG. 7A, Lane 5 & 6), α-lactalbumin (FIG. 7B, Lane 1, 2, & 3), and egg γ-globulin (FIG. 7B, Lane 4, 5, 6, & 7). Although protease Q showed its activity on keratin, it is not a keratinase, because keratinase uses oligopeptides, such as succinyl-Ala-Ala-Phe-Leu-p-nitroanilide (AAPF) (SEQ. ID. NO: 4) as a substrate (Nickerson and Durand, 1963), whereas protease Q does. Other than proteinase K, only a few microbial alkaline proteases possess keratinase activity. A not well-characterized protease from the fungus *Trichophyton mentagrophytes* has been reported to possess keratinase activity, but it has a molecular weight of 48.4 kD with an optimal reaction pH at 7.0 (Yu et al., 1969). Another alkaline protease from the fungus *Alkalophilic streptomyces* has also been reported to have keratinase activity, which has a molecular weight of 50 kD and is extremely alkalophilic with an optimal reaction pH higher than pH 12 (Nakanishi et al., 1974). In addition, all these enzymes are not SDS-resistant as described for protease Q below. In fact, protease Q has several properties similar to that of proteinase K. However, the N-terminal sequence and amino acid composition of protease Q shows that it has no relationship with proteinase K. Thus, protease Q is a new member of subtilisin family of serine proteases.

EXPERIMENT 12

Influence of SDS on the Proteolytic Activity of Protease Q

Figure 8:
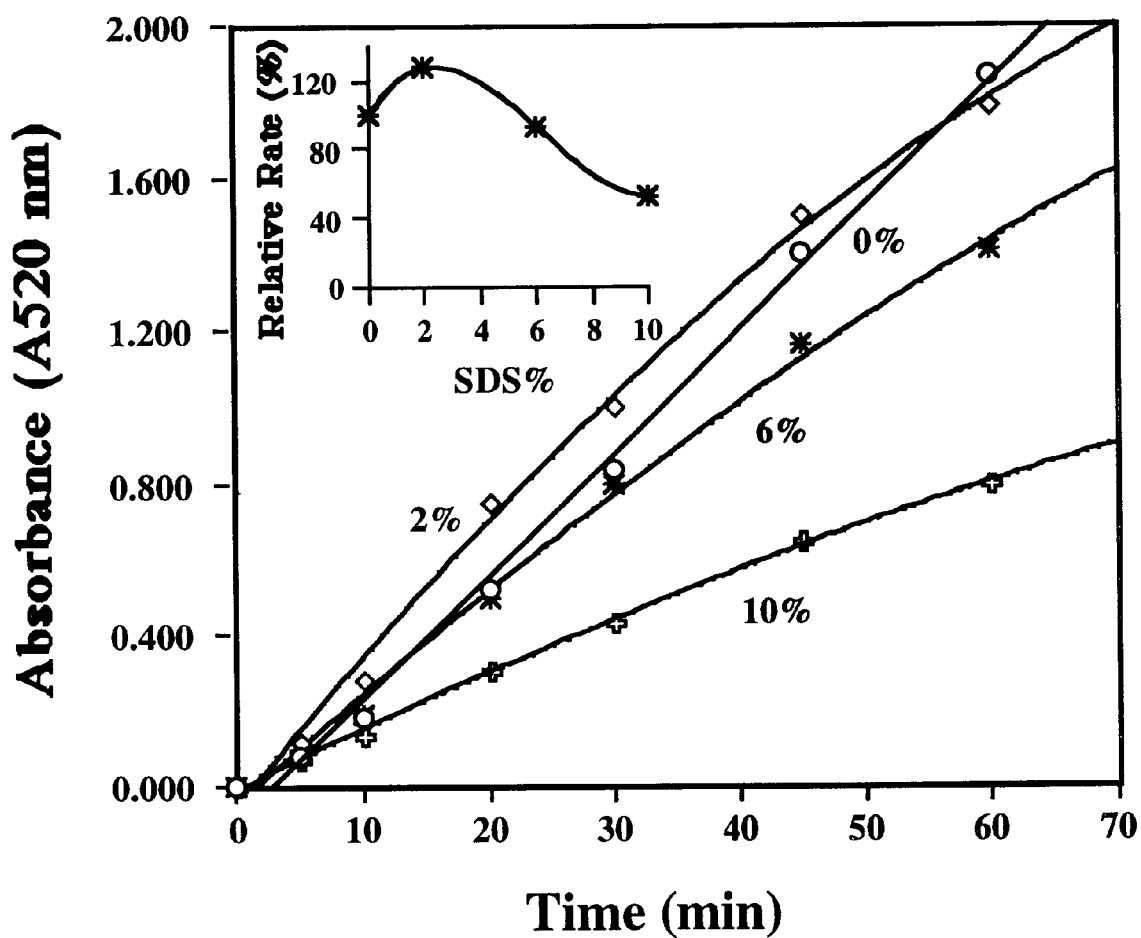
FIG. 8 is a graph showing the hydrolysis of Azocoll by protease Q at different sodium dodecyl sulfate (SDS) concentrations.

On native protein substrates, protease Q demonstrated its strong proteolytic activity with the presence of 2% (w/v) SDS in the reaction mixture as shown in both FIGS. 7A and 7B. In fact, the digestion products (i.e., polypeptide fragments formed as a result of digestion) formed in the presence of SDS had several lower molecular weight peptide fragments than in its absence, suggesting that protease Q was more active in 2% SDS than in buffer alone. Alternatively, the increased digestion of proteins in the presence of 2% SDS might be due to SDS-induced denaturation of the substrate proteins, which renders them to be better substrates for the enzyme. To elucidate if protease Q was not only more active but also stable in SDS solutions, its activity on Azocoll, an azo-dye impregnated collagen that is not denatured by and insoluble in SDS solutions, was studied at various SDS concentrations. The reaction conditions were similar to that in EXPERIMENT 4 except for the increasing concentration of SDS. The rates of hydrolysis of Azocoll by protease Q at various SDS concentrations are shown in FIG. 8. The results indicate that even in 10% SDS (w/v), protease Q was very active on Azocoll. Comparison of the initial rates of hydrolysis in various SDS concentrations indicate that protease Q was more active in buffer containing 2% SDS than in buffer alone. In 6% SDS, its activity decreased only slightly compared to that of the control. In 10% SDS, it retained about 47% of its original activity (with Azocoll as the substrate). Since Azocoll is an insoluble substrate even in the presence of SDS, the substrate denaturation theory can be ruled out. Thus, the activity of protease Q in 2–10% SDS truly reflects its remarkable stability in the detergent solution.

EXPERIMENT 13

Effect of SDS on the Proteolytic Activity of Protease Q on β-Casein and β-Lactoglobulin at Different SDS Concentrations The reaction conditions were similar to that described for EXPERIMENT 7. The β-casein concentration in the final reaction mixture was 1% in 0.1 M Tris-HCl buffer (pH 8.3) containing different SDS concentrations. The enzyme to substrate ratio in the reaction mixture was 5 units of enzyme (on the basis of casein as substrate in the absence of SDS) per mg of protein substrate. The reaction mixture was incubated for 30 min at 37° C. At the end of the reaction time, an aliquot of the reaction mixture was mixed with SDS-PAGE sample buffer containing 4% SDS and heated in a boiling water bath for 5 min to stop the reaction. The samples were then analyzed by SDS-PAGE (16.5% gel) as described in EXPERIMENT 6.

Figure 9A:
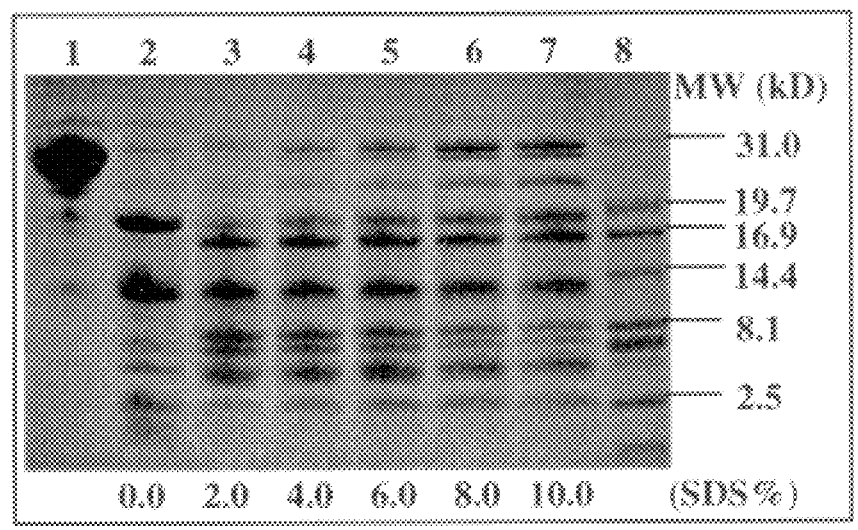
FIG. 9A is a SDS-PAGE gel showing the effect of SDS concentration on proteolytic digestion of β-casein by protease Q (Tricine-SDS-PAGE gel, 16.5% T).

FIG. 9A illustrates the effect of SDS on proteolytic activity of protease Q on β-casein. Lane 1 shows the β-casein control; lane 2 shows the β-casein treated with protease Q without SDS; and lanes 3 to 7 show β-casein treated with protease Q in the presence of SDS at 2, 4, 6, 8, and 10% (w/v) concentrations, respectively. Lane 8 is the molecular weight standards. It should be noted that β-casein was hydrolyzed by protease Q at all SDS concentrations. However, the intensity of the protein band corresponding to intact β-casein increased progressively with increase of SDS concentration, indicating that the activity of protease Q on β-casein decreased progressively with increase of SDS concentration.

To determine the relative activity of protease Q on β-casein at different SDS concentration, the relative intensity of the intact β-casein band at each SDS concentration was digitized by using an EL Lamp Dual Transilluminator (Fotodyne Inc., Hartland, Wis.) and quantified by using the COLLEGE Image Analysis software (version 3.1, University of Wisconsin-Madison, Wis.). Using the band intensity of the β-casein control (Lane 1) as a reference, the percentage of β-casein hydrolyzed at different SDS concentration represented the relative activity of protease Q at different SDS concentrations.

Figure 9B:
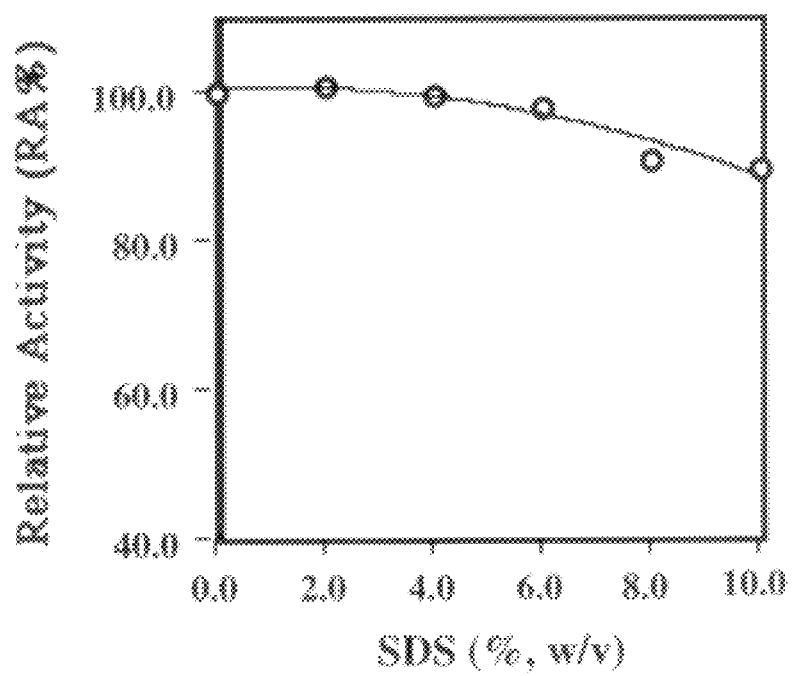
FIG. 9B is a graph showing the relative proteolytic activity of protease Q on β-casein at different SDS concentrations.
Figure 10:
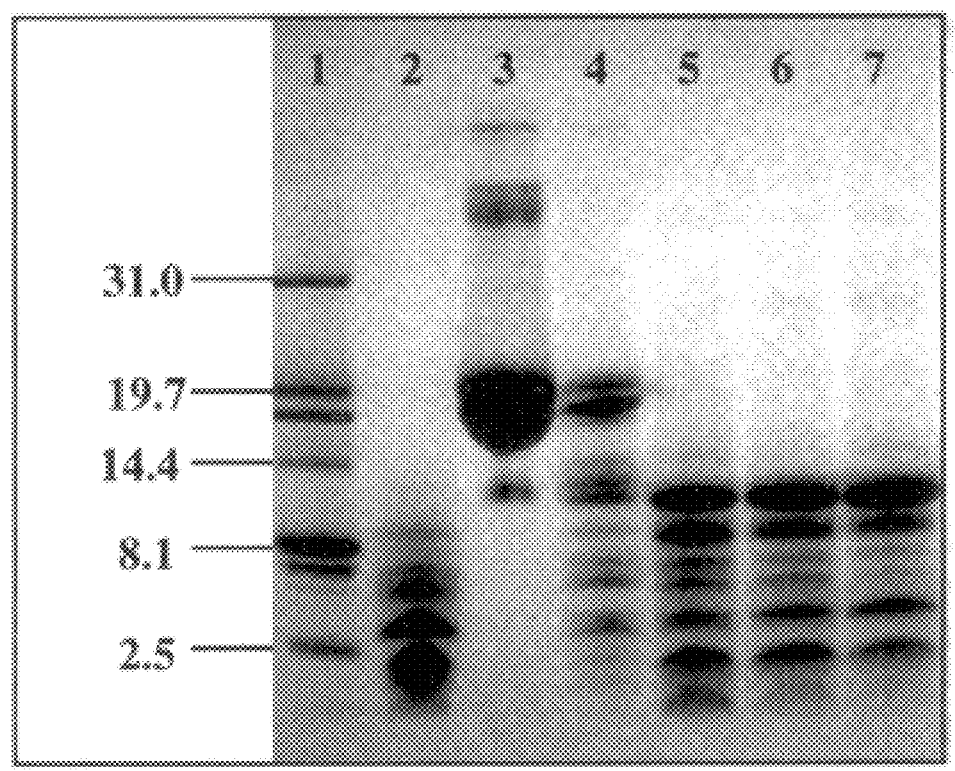
FIG. 10 is a SDS-PAGE gel showing the effect of SDS concentration on proteolytic digestion of β-lactoglobulin by protease Q.

FIG. 9B illustrates the relative proteolytic activity of protease Q on β-casein at different SDS concentration. The data show that about 87% of β-casein has been hydrolyzed in 10% SDS. The results of similar experiments with β-lactoglobulin are shown in FIG. 10. It should be noted that in this case, β-lactoglobulin was completely hydrolyzed by protease Q to small peptides even in 10% SDS solution.

EXPERIMENT 14

Comparison of Stabilities of Protease Q and Subtilisin Carlsberg in SDS at 25° C.

In this experiment, protease Q and subtilisin Carlsberg with similar activity units were incubated separately at 25°

Figure 11A:
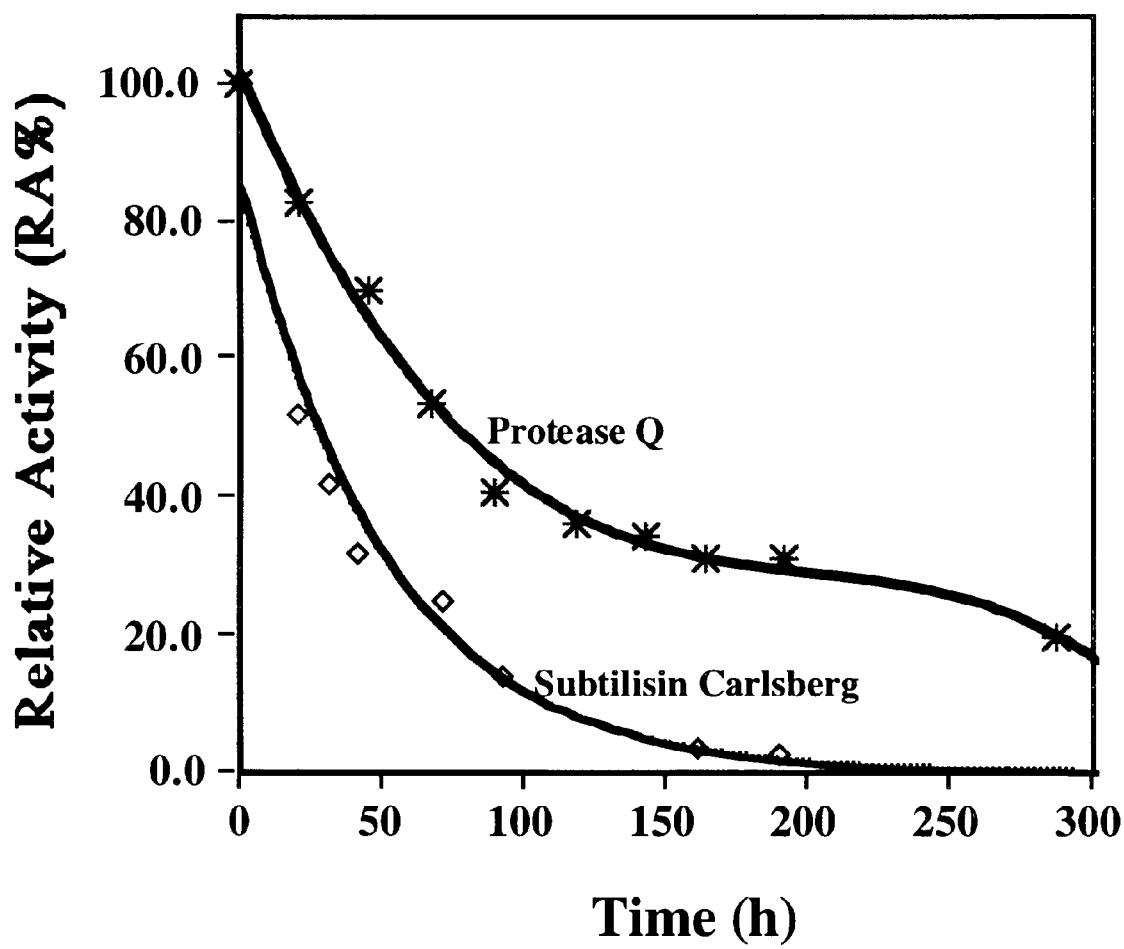
FIG. 11A is a graph showing differences in stabilities of protease Q and subtilisin Carlsberg in 5% SDS (w/v) at 25° C.
Figure 11B:
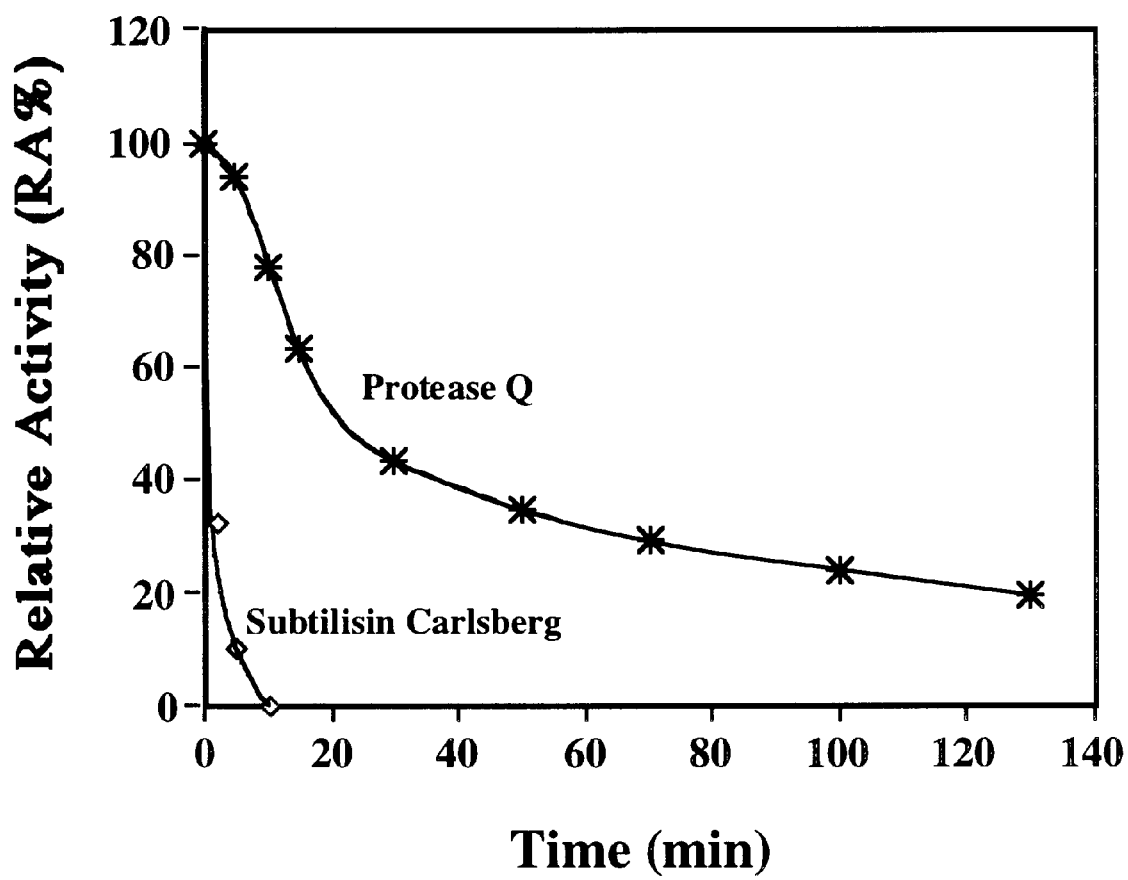
FIG. 11B is a graph showing differences in stabilities of protease Q and subtilisin Carlsberg in 5% SDS (w/v) at 50° C.

C. in 5% SDS in Tris-HCl buffer, pH 8.3. Aliquots were withdrawn at various time intervals and the remaining proteolytic activity was determined using succinyl-Ala-Ala-Pro-Phe-p-nitroanilide (AAPF) (SEQ. ID. NO: 4) as the substrate as described in EXPERIMENT 5. As illustrated in FIG. 11A, the half-life of protease Q in 5% SDS was about 75 hours, whereas that of subtilisin Carlsberg was only about 25 hours. FIG. 11B shows the stabilities of protease Q and subtilisin Carlsberg in 5% (w/v) SDS at 50° C. The half-life of protease Q in 5% SDS at 50° C. was about 20 min, whereas that of subtilisin Carlsberg was less than a minute. These results indicate that protease Q was more stable in SDS solutions than subtilisin Carlsberg.

EXPERIMENT 15

Stability of Protease Q Against Cationic Detergent Hexadecyl-trimethylammonium Bromide (HTAB)

Figure 12:
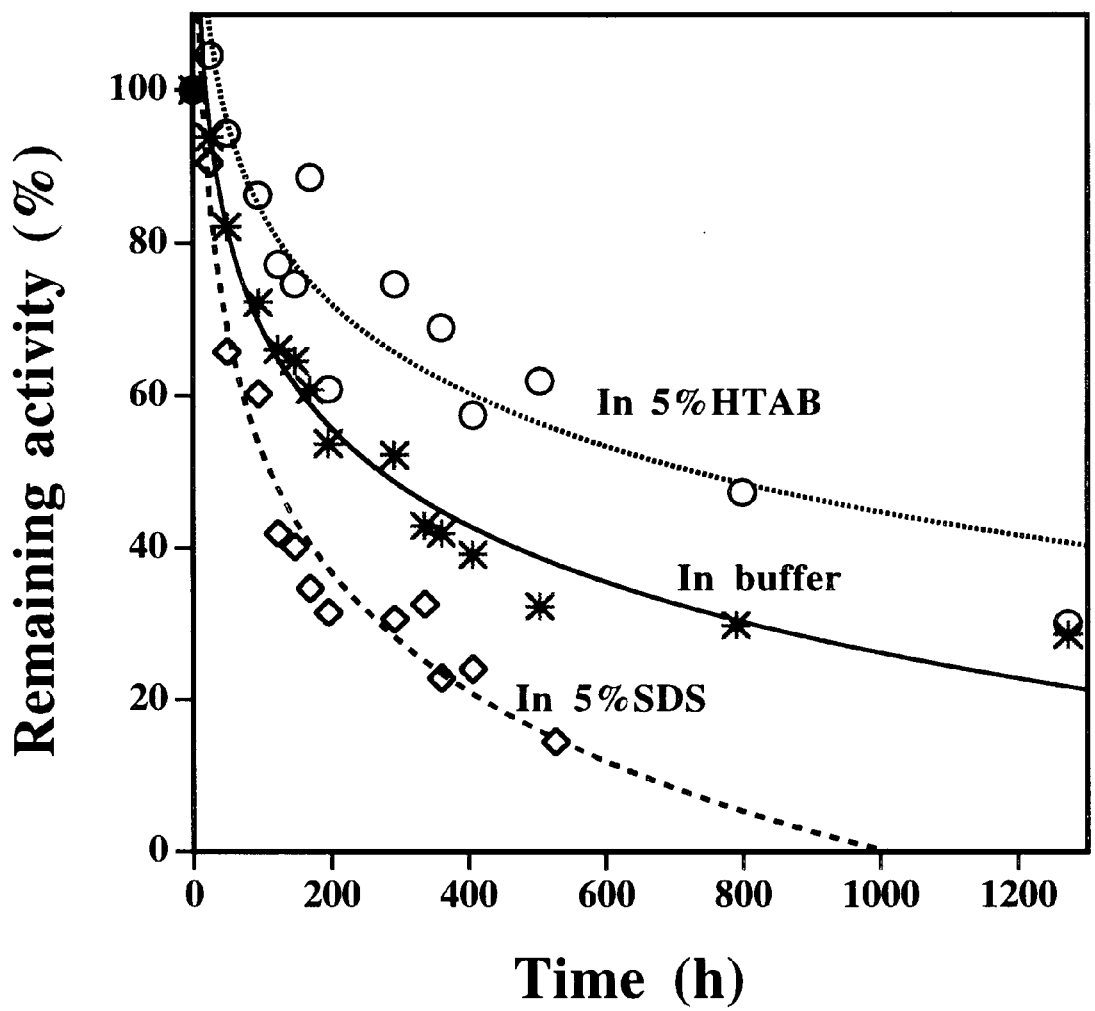
FIG. 12 is a graph showing stability of protease Q in a cationic detergent hexadecyl-trimethylammonium bromide (HTAB).

The stability of protease Q against a cationic detergent Hexadecyl-trimethylammonium bromide (HTAB) was also investigated and compared with the stability in SDS. The experimental conditions were similar to that in EXPERIMENT 14, but the incubation temperature was 37° C. instead of 25° C. As illustrated in FIG. 12, the half-life of protease Q in 5% HTAB was about 750 hours whereas that in 5% SDS was only about 75 hours. These results indicate that protease Q is more stable in cationic detergents such as HTAB than in anionic detergents such as SDS. It should also be noted that protease Q was relatively more stable in 5% HTAB than in buffer alone, implying that, like calcium ions, cationic detergents may stabilize the conformation of protease Q and protect it against autolysis.

EXPERIMENT 16

Proteolysis of β-lactoglobulin by Protease Q in the Presence of Urea

Figure 13:
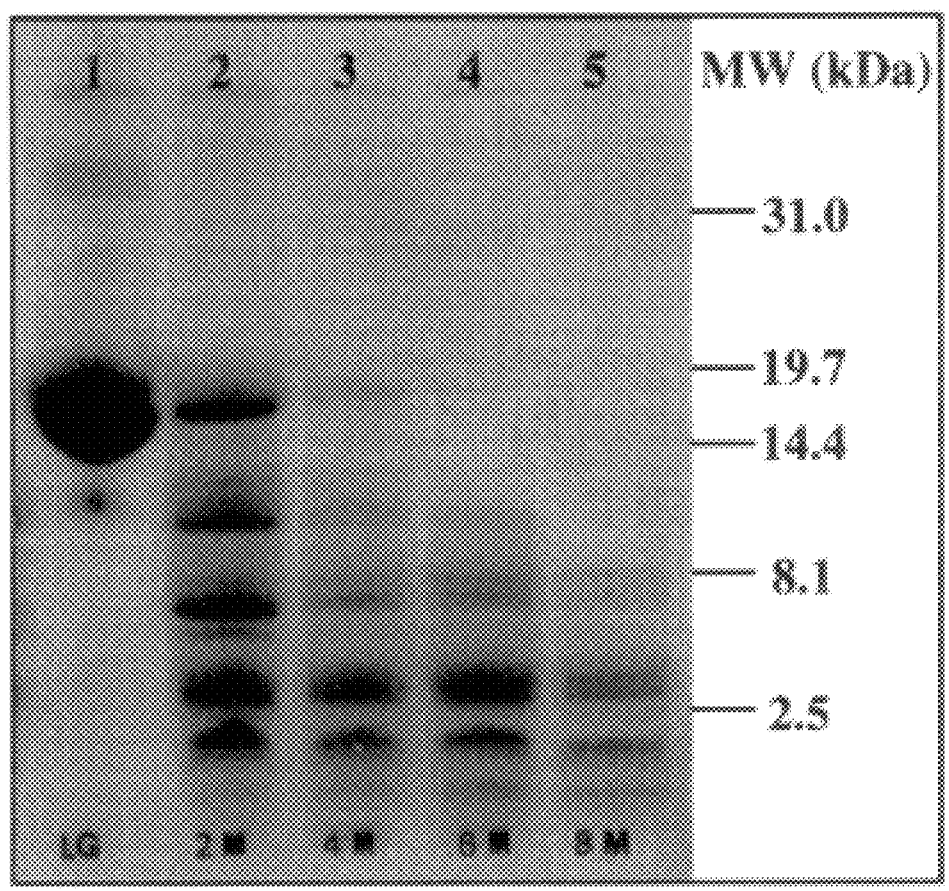
FIG. 13 is a SDS-PAGE gel showing the proteolytic digestion of β-lactoglobulin by protease Q in the presence of urea. (Tricine-SDS-PAGE gel 16.5% T).

FIG. 13 illustrates the proteolysis of β-lactoglobulin by protease Q in the presence of urea. The reaction conditions were similar to that described for EXPERIMENT 7. The β-lactoglobulin concentration in the final reaction mixture was 1% in 0.1 M Tris-HCl buffer (pH 8.3) containing different urea concentrations. The enzyme to substrate ratio in the reaction mixture was 8 units of enzyme (on the basis of casein as substrate in the absence of urea) per mg of protein substrate. The reaction mixture was incubated for 40 min at 37° C. At the end of the reaction time, an aliquot of the reaction mixture was mixed with SDS-PAGE sample buffer containing 4% SDS and heated in a boiling water bath for 5 min to stop the reaction. The samples were then analyzed by SDS-PAGE (16.5% gel) as described in EXPERIMENT 6. Lane 1 shows the β-lactoglobulin (LG) control; lanes 2, 3, 4, & 5 show LG hydrolyzed by protease Q in the presence of 2, 4, 6, and 8 M Urea, respectively in the reaction mixture. The extent of hydrolysis of intact β-lactoglobulin increased with increasing urea concentration, partly due to urea-induced denaturation of β-lactoglobulin which rendered it highly susceptible to proteolysis.

EXPERIMENT 17

Proteolysis of β-casein by Protease Q in the Presence of Urea

Figure 14:
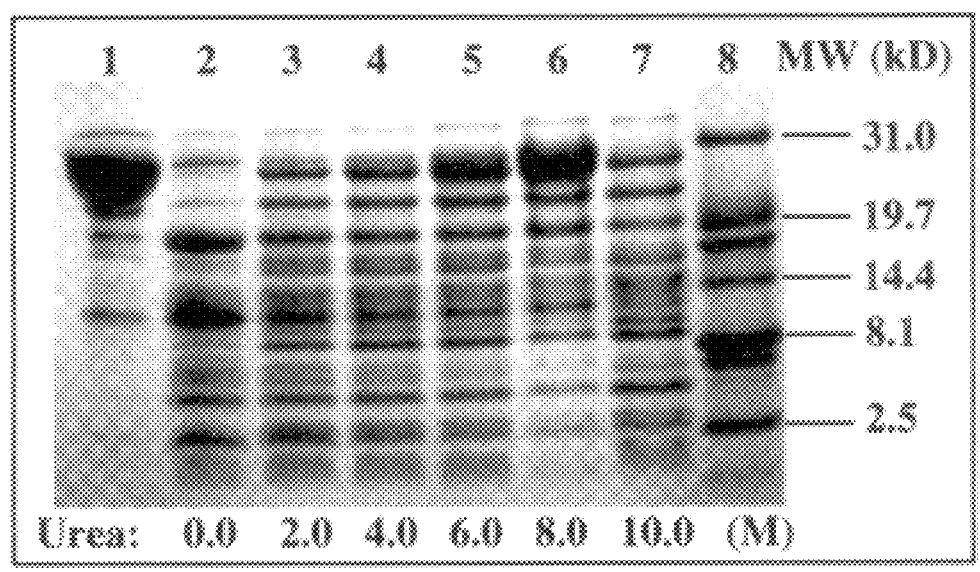
FIG. 14 is a SDS-PAGE gel showing the proteolytic digestion of β-casein by protease Q in the presence of urea. (Tricine-SDS-PAGE gel 16.5% T).

FIG. 14 illustrates effect of urea on proteolytic digestion of β-casein by protease Q. The reaction conditions were similar to that described for EXPERIMENT 7. The β-casein concentration in the final reaction mixture was 1% in 0.1 M Tris-HCl buffer (pH 8.3) containing different urea concentrations. The enzyme to substrate ratio in the reaction mixture was 5 units of enzyme (on the basis of casein as substrate in the absence of urea) per mg of protein substrate. The reaction mixture was incubated for 30 min at 37° C. At the end of the reaction time, an aliquot of the reaction mixture was mixed with SDS-PAGE sample buffer containing 4% SDS and heated in a boiling water bath for 5 min to stop the reaction. The samples were then analyzed by SDS-PAGE (16.5% gel) as described in EXPERIMENT 6. Lane 1 shows the β-casein control; lane 2 shows the β-casein treated with protease Q without urea; lanes 3 to 6 show β-casein treated with protease Q in the presence of urea at 2, 4, 6, and 8 M, respectively; lane 7 shows the freeze-dried protease Q (with 5× activity as previous lanes) and β-casein were added to 10 M urea; and lane 8 shows the protein markers. The data in FIG. 14 show that, unlike β-lactoglobulin, the extent of hydrolysis of β-casein decreased with increasing urea concentration. Nonetheless, even at 10 M urea concentration a significant amount of β-casein was hydrolyzed by protease Q. The results shown in FIGS. 13 and 14 clearly indicate that protease Q was relatively very stable in concentrated urea solutions.

The present invention is not limited to the embodiments described above, but encompasses all such embodiments falling within the scope of the claims following the Bibliography.

BIBLIOGRAPHY

U.S. Pat. No. 4,386,160 to Branner-Jorgensen

U.S. Pat. No. 5,346,822 to Vetter et al.

U.S. Pat. No. 5,427,936 to Moeller et al.

Bajorath, J.; Saenger, W. and Pal, G. P. 1988a. Autolysis and inhibition of proteinase K, a subtilisin-related serine proteinase isolated from the fungus *Tritirachium album* limber. *Biochim. Biophy. Acta* 954:176–182.

Bajorath, J.; Hinrichs, W. and Saenger, W. 1988b. The enzymatic activity of proteinase K is controlled by calcium. *Eur. J. Biochem.* 176, pp. 441–447.

Chavira, R.; Burnett, T.; and Hageman, J. H. 1984. Assaying proteinases with azocoll. *Anal. Biochem.* 136, pp. 446–450.

Deane, S. M., Robb, F. T. and Woods, D. R. 1987. *J. Gen. Micro.* 133, pp. 391–399.

DelMar, E. G., Largman, C., Brodrick, J. W. and Geokas, M. C. 1979. A sensitive new substrate for chymotrypsin. *Anal. Biochem.* 99, pp. 316–320.

Ebeling, W.; Hennrich, N.; Klockow, M.; Metz, H.; Orth, H. D. and Lang, H. 1974. Protease K from *Tritirachium album* limber, *Eur. J. Biochem.* 47:91–97.

Findley, J. B. C. and Geisow, M. J. 1989. *Protein Sequencing: A Practical Approach.* New York: IRL Press.

Frömmel, C. and Höhne, W. E. 1981. Influence of calcium binding on the thermal stability of thermitase, a serine protease from *Thermoactinomyces vulgaris. Biochim. Biophys. Acta* 670:25–31.

Gold, A. M. 1967. Sulfonylation with Sulfonyl Halides. In *Methods of Enzymology,* Hirs, C. H. W. (ed), Academic Press, New York. Vol.11, pp. 706–711.

Jany, K. D.; Lederer, G. and Mayer, B. 1986. Amino acid sequence of protease K from the mold *Tritirachium album* limber. *FEBS Letters* 199(2):139–144.

LeGendre, N.; Mansfield, M.; Weiss, A. and Matsudaira, P. 1993. In *A Practical Guide to Protein and Peptide Purification for Microsequencing",* Academic Press, San Diego, pp. 71–101.

Nakanishi, T. and Yamamoto, T. (1974). *Agric. Biol. Chem.* (Tokyo) 38, pp. 2391–2397.

Nickerson, W. J. and Durand, S. C. (1963). *Biochim. Biophy. Acta,* 77, pp. 87–99.

Ottesen, M. And Svendsen, I. 1970. In *Methods in Enzymology,* ed. E. Perlmann and L. Lorand, Academic Press, New York, vol. 19, pp. 199–215.

Powers, J. C. and Harper, J. W. 1986. In *Proteinase Inhibitors.* Barrett, A. J. And Salvesen, G. (ed), Elsevier Amsterdam, pp. 219–298.

Reimerdes, E. H. and Klostermeyer, H. 1976. In *Methods in Enzymology,* L. Lorand, Ed., Academic Press, New York. vol. 45, part B, pp. 26–28.

Schagger, H. and von Jagow, V. 1987. Tricine-Sodium Dodecyl Sulfate-Polyacrylamide Gel Electrophoresis for the Separation of Proteins in the Range from 1 to 100 kDa. *Anal. Biochem.* 166, pp. 368–379.

Smith, E. L.; DeLange, R. J.; Evans, W. H.; Landon, M. and Markland, F. S. 1968. Subtilisin Carlsberg. V. The Complete Sequence; Comparison with Sobtilisin BPN'; Evolutionary Relationships, *J. Biol. Chem.* 243:2184–2191.

Teorell, T.; and Stenhagen, E. 1938. *Biochem. Z.* 299, pp. 416–419.

Tsong, T. Y.; Hearn, R. P.; Wrathall, D. P. and Sturtevant, J. M. 1970. A calorimetric study of thermally induced conformational transitions of ribonuclease A and certain of its derivates. *Biochem.* 9:2666–2677.

Umezawa, H. 1976. Structures and activities of protease inhibitors of microbial origin. In *Methods of Enzymology.* Lorand, L. (ed), Academic Press, New York. Vol.45, pp. 678–695.

Voordouw, G. and Roch, R. S. 1975. The Role of Bound Calcium ions in Thermostable, Proteolytic Enzymes. I. Studies on Thermomycolase, the Thermostable Protease from the Fungus. *Biochem.* 14:4659–4666.

Yu, R. J., Harmon, S. R., Wachter, P. E. and Blank, F. (1969). *Arch. Biochem. Biophys.* 135, pp. 363–370.

---

We claim:

1. A purified alkaline protease derived from *B. pumilus* strain ATCC 202073, having an N-terminal amino acid sequence of A Q T V P Y G I P Q I K A P A V H A Q G Y K G A N V K V A V (SEQ. ID. NO: 1).

2. The protease of claim 1, which has an isoelectric point (pI) of 9.35.

3. The protease of claim 1, which is composed of 309 amino acids.

4. The protease of claim 1, which has a molecular weight of 31,100 daltons.

5. The protease of claim 1, which retains at least 50% of its activity at pH values from 5.0 to 12.0.

6. A purified alkaline protease obtained from *Bacillus pumilus* strain ATCC 202073 and which has the following properties:

a. isoelectric point (pI): 9.35;
    b. number of amino acids: 309;
    c. N-terminus sequence: A Q T V P Y G I P Q I K A P A V H A Q G Y K G A N V K V A V (SEQ. ID. NO: 1);
    d. molecular weight: 31,100 daltons; and
    e. retains at least 50% of its activity at pH values from 5.0 to 12.0.

7. A cleaning composition containing the purified alkaline protease of claim 1 in combination with a liquid or solid detergent carrier and at least one conventional surface active detergent ingredient.

8. The cleaning composition of claim 7, further comprising one or more detergent additives selected from the group consisting of intensifiers, enzyme stabilizers, anti-redeposition agents, complexing agents, chelating agents, foam regulators, optical brighteners, opacifying agents, corrosion inhibitors, anti-electrostatic agents, dyes, bactericides, bleaching agent activators, and peracid bleaching agent precursors.

* * * * *

SEQUENCE LISTING

```
(1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1:

Ala Gln Thr Val Pro Tyr Gly Ile Pro Gln Ile Lys Ala Pro Ala Val
1               5                  10                  15

His Ala Gln Gly Tyr Lys Gly Ala Asn Val Lys Val Ala Val
            20                  25                  30

(2) INFORMATION FOR SEQ ID NO:2:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Ala Gln Ser Val Pro Tyr Gly Val Ser Gln Ile Lys Ala Pro Ala Leu
1               5                  10                  15

His Ser Gln Gly Tyr Thr Gly Ser Asn Val Lys Val Ala Val
            20                  25                  30

(2) INFORMATION FOR SEQ ID NO:3:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide
```

-continued (xi) SEQUENCE DESCRIPTION: SEQ ID NO:3:

```
Ala Gln Thr Val Pro Tyr Gly Ile Pro Leu Ile Lys Ala Asp Lys Val
1               5                   10                  15

Gln Ala Gln Gly Phe Lys Gly Ala Asn Val Lys Val Ala Val
                20                  25                  30
```

(2) INFORMATION FOR SEQ ID NO:4:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Ala Ala Pro Phe